(12) United States Patent
Huang et al.

(10) Patent No.: US 7,262,276 B2
(45) Date of Patent: Aug. 28, 2007

(54) ANTI HUMAN OVARIAN CANCER-ANTI CD3 BISPECIFIC ANTIBODY

(75) Inventors: Hualiang Huang, Beijing (CN); Xin Jiang, Beijing (CN); Min Fang, Beijing (CN); Xiaocong Yu, Beijing (CN); Jie Feng, Beijing (CN); Ping Zhou, Beijing (CN); Qing Lin, Beijing (CN)

(73) Assignee: Beijing ABT Genetic Engineering Technology Co. Ltd., Beijing (CN)

( * ) Notice: Subject to any disclaimer, the term of this patent is extended or adjusted under 35 U.S.C. 154(b) by 201 days.

(21) Appl. No.: 10/478,345

(22) PCT Filed: May 23, 2002

(86) PCT No.: PCT/CN02/00347

§ 371 (c)(1),
(2), (4) Date: Nov. 21, 2003

(87) PCT Pub. No.: WO03/004648

PCT Pub. Date: Jan. 16, 2003

(65) Prior Publication Data

US 2005/0255115 A1    Nov. 17, 2005

(30) Foreign Application Priority Data

May 24, 2001    (CN) ................................ 01 1 18247

(51) Int. Cl.
*C07K 16/30* (2006.01)

(52) U.S. Cl. .................. 530/387.3; 530/387.7

(58) Field of Classification Search ............. 530/387.1, 530/387.7
See application file for complete search history.

(56) References Cited

U.S. PATENT DOCUMENTS

| 6,027,725 A |   | 2/2000 | Whitlow et al. ......... 424/136.1 |
| 6,132,992 A | * | 10/2000 | Ledbetter et al. .......... 435/69.7 |
| 6,146,628 A |   | 11/2000 | Uckun et al. ............ 424/134.1 |

FOREIGN PATENT DOCUMENTS

| EP | 0505908 | 9/1992 |
| WO | 93/16185 | 8/1993 |
| WO | 03/04648 | 1/2003 |

OTHER PUBLICATIONS

Kriangkum et al (Hybridoma, 2000, 19:33-41).*
Kriangum et al (Hybridoma, Feb. 2000, 19:33-41).*
Marken et al (J of Biological Chemistry, 1994, 269, 73977401).*

* cited by examiner

*Primary Examiner*—Shanon Foley
*Assistant Examiner*—Laura B Goddard
(74) *Attorney, Agent, or Firm*—Jones Day

(57) ABSTRACT

The present invention provides an anti-ovarian cancer bispecific antibody. Said antibody includes two polypeptide domains connected by a polypeptide linker, one is anti-ovarian cancer antibody, or its Fab fragment, single complementarity determining region (CDR) antibody or single chain Fv (scFv) and the other is anti-CD3 antibody, or its Fab fragment, single CDR antibody or scFv. The present invention also provides DNA sequences encoding said antibody, an expression vector containing said DNA sequence, and a host cell containing said expression vector.

15 Claims, 13 Drawing Sheets

```
    Glu Val Gln Leu Gln Glu Ser Gly Pro Glu Val Lys Lys Pro Gly
  1 GAG GTG CAG CTG CAG GAG TCT GGA CCT GAG GTG AAG AAG CCT GGA
    Glu Thr Val Arg Ile Ser Cys Lys Ala Ser Gly Tyr Thr Phe Thr
 46 GAG ACA GTC AGG ATC TCC TGC AAG GCT TCT GGG TAT ACC TTC ACA
    Thr Ala Gly Met Gln Trp Val Gln Lys Met Pro Gly Lys Gly Leu
 91 ACT GCT GGA ATG CAG TGG GTG CAA AAG ATG CCA GGA AAG GGT TTG
    Lys Trp Leu Gly Trp Ile Asn Thr Asn Ser Glu Val Pro Lys Tyr
136 AAG TGG CTT GGC TGG ATA AAC ACC AAC TCT GAA GTT CCA AAA TAT
    Ala Glu Asp Phe Arg Gly Arg Phe Ala Phe Ser Leu Glu Thr Ser
181 GCA GAA GAC TTC AGG GGA CGG TTT GCC TTC TCT TTG GAG ACC TCT
    Ala Ser Thr Ala Tyr Leu Gln Ile Ser Asn Leu Lys Asn Glu Asp
226 GCC AGC ACT GCA TAT TTA CAG ATA AGC AAC CTC AAA AAT GAG GAC
    Thr Ala Thr Phe Phe Cys Ala Arg Ser Phe Thr Trp Gly Thr Met
271 ACG GCT ACG TTT TTC TGT GCG AGA TCT TTT ACT TGG GGG ACT ATG
    Asp Tyr Trp Gly Gln Gly Thr Thr Val Thr Val Ser Ser
316 GAC TAT TGG GGG CAA GGG ACC ACG GTC ACC GTC TCC TCA
```

The nucleotide sequence and amino acid sequence of VH against human ovarian cancer

```
    Asp Val Val Met Thr Gln Thr Pro Leu Ser Leu Pro Val Ser Leu
  1 GAT GTT GTG ATG ACC CAA ACT CCA CTC TCC CTG CCT GTC AGT CTT
    Gly Asp Gln Ala Ser Ile Ser Cys Arg Ser Ser Gln Thr Leu Val
 46 GGA GAT CAA GCC TCC ATC TCT TGC AGA TCT AGT CAG ACC CTT GTA
    His Ser Ile Gly Asn Thr Tyr Leu His Trp Tyr Leu Gln Lys Pro
 91 CAC AGT ATT GGA AAC ACC TAT TTA CAT TGG TAC CTG CAG AAG CCA
    Gly Gln Ser Pro Lys Leu Leu Ile Tyr Lys Val Ser Asn Arg Phe
136 GGC CAG TCT CCA AAA CTC CTG ATC TAC AAG GTT TCC AAC CGA TTT
    Ser Gly Val Pro Asp Arg Phe Ser Gly Ser Gly Ser Gly Thr Asp
181 TCT GGG GTC CCA GAC AGG TTC AGT GGC AGT GGA TCA GGG ACA GAT
    Phe Thr Leu Lys Ile Ser Arg Val Glu Ala Glu Asp Leu Gly Val
226 TTC ACA CTC AAG ATC AGC AGA GTG GAG GCT GAG GAT CTG GGA GTT
    Tyr Phe Cys Ser Gln Ser Thr His Val Pro Tyr Thr Phe Gly Gly
271 TAT TTC TGC TCT CAA AGT ACA CAT GTT CCG TAC ACG TTC GGA GGG
    Gly Thr Lys Leu Glu Leu Lys
316 GGG ACC AAG CTG GAG CTC AAA
```

The nucleotide sequence and amino acid sequence of VL against human ovarian cancer

Figure 2

```
      Gln  Val  Gln Leu Val Gln Ser Gly Ala Glu Val Arg Lys Pro Gly
  1 CAG GTT CAG TTG GTG CAG TCT GGC GCT GAG GTG AGG AAG CCT GGG
         Ala Ser Val Arg Val Ser Cys Lys Ala Ser Gly Tyr Thr Phe Thr
 46    GCA TCA GTG AGG GTC TCC TGC AAG GCT TCT GGA TAC ACC TTC ACC
       Arg Tyr Thr Met His Trp Val Arg Gln Ala Pro Gly His Gly Leu
 91    CGT TAC ACT ATG CAC TGG GTG CGT CAG GCC CCT GGG CAC GGG CTT
       Glu Trp Ile Gly Tyr Ile Asn Pro Ser Arg Gly Tyr Thr Asn Tyr
136    GAG TGG ATT GGA TAC ATT AAC CCT TCC AGA GGG TAC ACT AAC TAC
       Asn Gln Lys Phe Lys Asp Arg Val Thr Met Thr Thr Asp Lys Ser
181    AAC CAA AAA TTC AAA GAT AGA GTG ACC ATG ACC ACT GAC AAA TCC
       Phe Ser Thr Ala Ile Met Asp Leu Arg Ser Leu Arg Ser Asp Asp
226    TTC AGT ACA GCC ATC ATG GAC CTG AGA AGT CTG AGA TCT GAC GAC
       Ser Ala Val Tyr Tyr Cys Ala Arg Tyr Tyr Asp Asp His Tyr Cys
271    TCG GCC GTG TAC TAC TGT GCT AGA TAC TAC GAC GAC CAC TAC TGC
       Leu Asp Tyr Trp Gly Gln Gly Thr Thr Val Thr Val Ser Ser
316 TTG GAT TAC TGG GGT CAA GGA ACC ACG GTC ACC GTC TCC TCA
```

The nucleotide sequence and amino acid sequence of reshaped VH against CD3

```
       Glu Ile Val Leu Thr Gln Ser Pro Ala Thr Leu Ser Leu Ser Pro
  1    GAG ATC GTA CTG ACC CAG TCT CCA GCC ACC CTG TCT TTG TCT CCA
       Gly Glu Arg Ala Thr Leu Ser Cys Ser Ala Ser Ser Ser Val Ser
 46    GGG GAA AGA GCC ACC CTC TCC TGC TCC GCA TCT TCC TCC GTT TCC
       Tyr Met Asn Trp Tyr Gln Gln Lys Pro Gly Gln Ala Pro Arg Arg
 91    TAC ATG AAC TGG TAC CAA CAG AAA CCT GGT CAA GCT CCT AGA AGA
       Trp Ile Tyr Asp Thr Ser Lys Leu Ala Ser Gly Ile Pro Ala Arg
136    TGG ATC TAT GAC ACC TCC AAA CTA GCA AGT GGT ATC CCA GCT AGG
       Phe Ser Gly Ser Gly Ser Gly Thr Asp Phe Thr Leu Thr Ile Ser
181    TTC AGT GGC AGT GGA TCA GGA ACA GAT TTC ACT CTC ACC ATC AGT
       Ser Leu Glu Pro Glu Asp Phe Ala Thr Tyr Tyr Cys Gln Gln Trp
226    AGC CTA GAG CCT GAA GAT TTT GCG ACT TAT TAT TGT CAG CAA TGG
       Ser Ser Asn Pro Phe Thr Phe Gly Gly Gly Thr Lys Val Glu Ile
271    TCT TCC AAC CCG TTC ACC TTC GGC GGA GGG ACT AAA GTG GAG ATC
       Lys Arg
       AAA CGA
```

The nucleotide sequence and amino acid sequence of reshaped VL against CD3

Figure 5

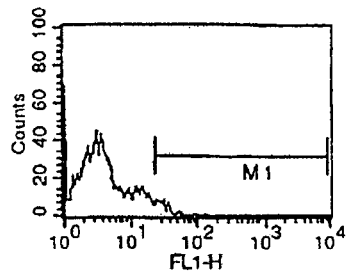
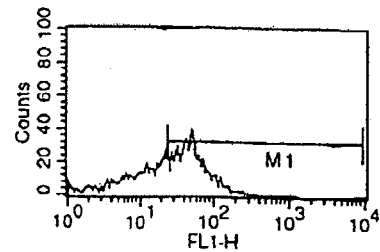

| Marker | Left,Right | Events | %Gated | %Total | Mean |
|---|---|---|---|---|---|
| All | 1,9647 | 3078 | 100.00 | 76.95 | 6.38 |
| M1 | 23,8977 | 156 | 5.07 | 3.90 | 32.43 |

| Marker | Left,Right | Events | %Gated | %Total | Mean |
|---|---|---|---|---|---|
| All | 1,9647 | 1559 | 100.00 | 77.95 | 37.06 |
| M1 | 23,8977 | 940 | 60.30 | 47.00 | 54.51 |

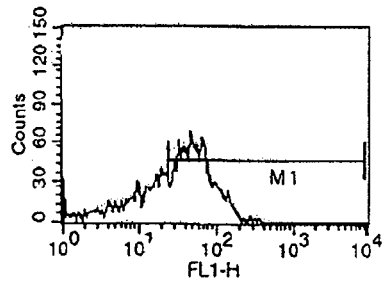
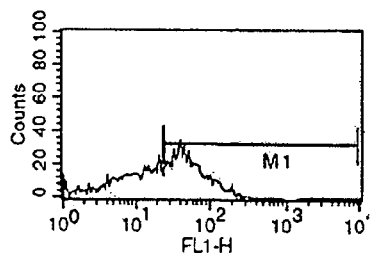

| Marker | Left,Right | Events | %Gated | %Total | Mean |
|---|---|---|---|---|---|
| All | 1,9647 | 2954 | 100.00 | 73.85 | 45.06 |
| M1 | 23,8977 | 1988 | 67.30 | 49.70 | 61.50 |

| Marker | Left,Right | Events | %Gated | %Total | Mean |
|---|---|---|---|---|---|
| All | 1,9647 | 1524 | 100.00 | 76.20 | 37.17 |
| M1 | 23,8977 | 855 | 56.10 | 42.75 | 58.20 |

Up left: negative control   Down left: positive control   Up right: the renatured reshaped scFv against CD3(0. 35ug/ml)   Down right: the renatured reshaped scFv against CD3(0. 70 ug/ml)

Figure 6

The synthesized sequence of multicloning site as follows:

MCS
NdeI XhoI    EcoRI   SacI        BamHI His His   His   His His   His        PstI
5'T<u>ATG</u>CTCGAGGAATTCGAGCTCACGGGATCCCATCACCATCACCATCAC<u>TAA</u>CTGCA3'
    ACGAGCTCCTTAAGCTCGAGTGCCCTAGGGTAGTGGTAGTGGTAGTGATTG

Fc interlinker:

```
     Asn Ser Thr Tyr Arg Val Val Ser Val Leu
  1  AAC AGC ACG TAC CGG GTT GTA AGC GTC CTC
     TTG TCG TGC ATG GCC CAA CAT TCG CAG GAG
     Thr Val Leu His Gln Asp Trp Leu Asn Gly
 31  ACC GTA CTG CAC CAG GAC TGG CTG AAT GGC
     TGG CAT GAC GTG GTC CTG ACC GAC TTA CCG
     Lys Glu Tyr Lys Cys Lys
 61  AAG GAA TAC AAA TGC AAG
     TTC CTT ATG TTT ACG TTC
```

HSA interlinker:

```
     Phe Gln Asn Ala Leu Leu Val Arg Tyr Thr
  1  TTC CAG AAT GCG CTG TTA GTT CGT TAC ACC
     AAG GTC TTA CGC GAC AAT CAA GCA ATG TGG
     Lys Lys Val Pro Gln Val Ser Thr Pro Thr
 31  AAG AAA GTA CCC CAA GTG TCA ACT CCA ACT
     TTC TTT CAT GGG GTT CAC AGT TGA GGT TGA
     Leu Val Glu Val Ser
 61  CTT GTA GAG GTC TCA
     GAA CAT CTC CAG AGT
```

205C' interlinker:

```
     Ala Ser Ala Asp Asp Ala Lys Lys Asp Ala
  1  GCT AGC GCA GAC GAT GCC AAA AAA GAT GCA
     CGA TCG CGT CTG CTA CGG TTT TTT CTA CGT
     Ala Lys Lys Asp Asp Ala Lys Lys Asp Asp
 31  GCT AAA AAA GAC GAT GCC AAA AAG GAC GAC
     CGA TTT TTT CTG CTA CGG TTT TTC CTG CTG
     Ala Lys Lys Asp Leu
 61  GCC AAA AAA GAT CTG
     CGG TTT TTT CTA GAC
```

Figure 8

ANTI HUMAN OVARIAN CANCER-ANTI CD3 BISPECIFIC ANTIBODY

BACKGROUND OF THE INVENTION

1. Field of the Invention

The present invention relates to an anti-cancer bispecific antibody constructed by gene engineering, nucleotide sequences encoding the said bispecific antibody, the expression vectors containing the said nucleotide sequences and host cells containing the vectors.

2. Description of the Related Art

Different from natural antibodies, two antigen-binding sites of bispecific antibody (BsAb) bear different specificities, therefore, it is bivalent in chemical structure but monovalent in binding function. BsAb directed to both tumor-associated antigens and trigger molecules on effector cells can recruit the immunological effector cells to tumor sites efficiently and activate them to kill tumor cells specifically. BsAbs are hybrid proteins that can be generated by chemical cross-link, hybridoma technology or genetic methods. In the chemical cross-link method, two kinds of monoclonal antibodies and fragments thereof were dissociated by reductants to generate monovalent antibodies and fragments thereof. The resulting BsAb is constructed via chemical cross-linking of two monovalent antibodies and fragments thereof from different parental antibodies. This strategy can be used for rapid production of BsAb in large scale but BsAb can be inactivated sometimes during cross-link and it is difficult to guarantee the homogeneity of products. Another strategy for production of BsAb is hybridoma technology by which an established hybridoma cell line secreting one monoclonal antibody was fused to spleen cells immunized with the other antigen or two established hybridoma cell lines secreting two different monoclonal antibodies were fused each other to create hybrid hybridomas. The former resulting hybridoma is called dimeric hybridoma and tetrameric hybridoma. Generally, BsAb produced by hybridoma technology keeps high bioactivities. However, the procedures are tedious and time-consuming and it is not easy to isolate BsAb from other non-active and unwanted antibodies generated simultaneously. These BsAb formats encountered another predictable problems: too large size and murine components contained in BsAb are immunogenic in patients and will induce the production of human anti-mouse antibodies (HAMA), which may prevent reuse of these BsAbs in clinic. Furthermore, production and purification of these formats of BsAb are expensive, which limits the application of BsAbs in clinic. Replacement of these traditional methods with gene recombination approaches has accelerated progress in this area. Based on the technology of small molecular antibodies, production of BsAb by gene engineering has advantages over those described above, such as the stability of process, large scale production, low cost and easy-to-use. Gene engineering has led to the development of various small molecular BsAb formats by connecting two different kinds of scFvs. There are three kinds of BsAb formats classified by different links. (1) mini-antibodies are heterodimers assembled by connecting two scFv fragments together with an oligomerized domain (e.g. leucine zipper motifs derived from Fos or Jun transcription factors). (2) Diabodies are non-covalently associated dimmers which are assembled by two single chains VH1-VL2 and VH2-VL1, both connected by a short linker that is too short to allow pairing between V-domains from the same chain. Thus, each chain alone is not capable of binding antigen, but co-expression of two chains ($VH_1$-$VL_2$ and $VH_2$-$VL_1$) leads to assembly of heterodimeric diabodies which can bind to two kinds of antigens. (3) ScBsAb: a interlinker was used for connecting two different scFvs with different specificities and ScBsAb was expressed in the host cells as a single polypeptide. The intralinker between two domains within scFv is often $(Gly_4Ser)_3$. As for the interlinker between two scFvs, there are two strategies for designing it. For the purpose of avoiding false paring between heterogenous variable regions, the interlinker is often a short peptide linker less than ten amino acid residues such as $Gly_4Ser$. Another strategy is to select a longer linker for the interlinker. In our lab, an interlinker with 25 amino acids named 205c', devised by Gruber in construction anti-TCR×anti-fluorescent scBsAb, was cited for one of three interlinkers. Another two interlinkers named Fc (26 residues) and HSA were devised, which both result in the proper folding of two scFvs and the formation of BsAb with two antigen-binding sites with high activities. In a word, the most important for designing interlinkers is to ensure the proper pairing between variable domains and folding of proteins, resulting in the formation of BsAb which maintains biological activities and stability. Some novel properties for facilitating purification and extending the plasma half-life time should be introduced.

BsAb-mediated immunotherapy plays a promising role in the clinical biotherapy for tumors. The following is two characteristics of BsAb. First, tumor-killing effects mediated by BsAb are based on stimulating the immune system, highly specific with tumors and free of MHC restriction. Second, due to lacking Fc domain, BsAb is harmless to normal tissues. Therefore, BsAb-mediated therapy is the complementarity of traditional methods such as surgery, radiotherapy and chemotherapy. The major effect of this approach is based on clearing up sub-clinical residuals and preventing or eliminating the tumor from recurrence and metastasis. BsAb can not only cure tumors but also stimulate the immune system to provide and keep the immune protection for a long time. Based on results of experiments in mouse and clinic, BsAb prepared for trial use should have at least five characteristics as follows: ① It targets to the relevant tumor antigens with high specificity and affinity; ② It can bind monovalently to trigger factors on effector cells-cytotoxic cells and result in cross link only when BsAb binds to tumor antigens due to lack of Fc domain; ③ BsAb is able to promote the effective cytotoxicity and inflammation selectively produced by the corresponding group of leukocytes at tumor sites; ④ BsAb must be humanized to minimize induction of human anti-mouse response following repeated uses; Finally, ⑤ BsAb should be not only small enough to penetrate into tumors but also large enough to keep in the circulation for a sufficient time.

Based on these points described above, numerous BsAbs triggering many kinds of immune effector cells and targeting different tumor cells have been developed in the past few years, wherein the effector cells include T lymphocytes, NK cells, monocytes, macropghages, neutrophils, LAK cells (lymphokine-activated cytotoxic cells) and TIL cells (tumor infiltrating lymphocytes) etc. T cells are commonly recognized as the major specific cells for immune responses. CD3 expressed on the surface of all mature T cells is the common surface marker for T cells. CD3 binds to TCR non-covalently, forming the whole TCR-CD3 complex, and involves in immune responses against antigen stimulus. Now CD3 is surface trigger molecule on immune effector cells used most widely and successfully. Following anti-CD3 antibody within BsAb binds to CD3 molecule on the surface of T cells, numerous effects as follows will be produced to kill tumor cells. These effects include: (1) proliferation and differentiation of T cells. Firstly, BsAb can activate the rest T cells, resulting in Th cell and Tc cell derived from the premature effector T cells with $CD4^+$ or $CD8^+$. Secondly, BsAb can activate numerous memory cells to proliferate and differentiate into effector T cells which will attack and kill tumor cells. The number of effector cells is directly related to the rate of tumor elimination. (2) release of cytokines: $CD4^+$ Th cells activated by BsAb can secrete a great deal of IL-2. IL-2 not only stimulates the proliferation of Th cells in autocrine, but also activates naive $CD8^+$ T cells in paracrine to become Tc cells, resulting in enlargement of cytotoxicity of Tc cells. In addition, IL-2 is a costimulating signal for activating T cells. Therefore, IL-2 plays a vital role in BsAb-mediated immune effects. Some other cytokines, such as TNF-$\alpha$ and IFN—Y are produced in the process of T-cell activation and can produce 'stander-by' effect by inhibiting the growth of 'stander-by' tumor cells through the medium among cells. (3) cytotoxicity: In vitro experiments indicate that mediated by BsAb, $CD8^+$ Tc interacts with tumor cells directly, releases cytotoxic materials through granule exocytosis and lyses target cells, which takes place rapidly usually within 4-6 hours following targeting tumor cells. The major components in the cytotoxic materials are perforin and serine easterases or granzymes. Perforins can attack the plasma membrane and form ion channels, thus causing entry of plenty of ions and water, resulting in the lysis and necrosis of cells while granzymes are similar to lymphotoxin, capable of activating DNases in the cell, thus causing lysis of nucleic DNA, resulting in the apoptosis of target cells.

Currently, Fv fragment is widely used for construction of BsAb, since it is the minimal unit with the complete antigen-binding site, small (about ⅙ of the whole antibody), absence of Fc domain, lower immunogenicity, easily penetration into the wall of blood vessels and solid tumors, easily expressed in *E. coli* and lower production cost. However, Fv is unstable and easy to dissociate in vivo because the covalent bond between VH and VL domains is unable to generate. In order to improve the stability of Fv fragment, a polypeptide intralinker between VH and VL domains is used to form so called ScFv. The intralinker is commonly a short flexible peptide with 15 amino acid residues in length such as $(Gly_4Ser)_3$. In the present invention, the said intralinker was used in both ScFvs. As mentioned above, there are several methods to construct BsAb. In the present invention, we constructed the single-chain bispecific antibody (ScBsAb) connected by an interlinker. The general principle for designing interlinkers is to ensure the proper pairing and folding of variable domains from two antibodies, furthermore keep the biological activities and stability of the said antibody. In addition, the said interlinker should endow BsAb some novel properties, such as easy purification and prolonged half-life time in the plasma etc. Two kinds of interlinkers, Fc and HSA originally designed in the present invention as a useful provide a novel idea for designing interlinkers. 205c' interlinker cited from literature was used to compare and verify the efficacy of interlinkers designed in the present invention and the value of the said design in construction of anti-ovarian BsAb. (1) Design of Fc interlinker: in order to minimize the immunogenicity and molecule size, small molecular antibodies are absent of Fv domains resulting in lack of several biological function, such as ADCC, CDC and the classic complement activating pathway. To resolve this problem, we devised the interlinkers to make up the said shortcoming of genetically engineered antibodies. IgG1 is the most potent molecule in inducing ADCC and CDC among four subtypes of IgGs. It can induce the classic complement activating pathway by combining to C1q with its C-terminal sequence of $CH_2$, wherein Gly318, Lys320 and Lys322 sites locate in the surface of Fc molecule to form a cluster in conformation and combine to C1q directly. In addition, Asn297 of $CH_2$ contains a glycosylation site which is vital to the effect of ADCC and CDC induced by Fc. Thus, a fragment from 297 to 322 of $CH_2$ in human IgG was selected to construct the interlinker of ScBsAb. It has 26 residues in length and contains the glycosylation site Asn297, the C1q-binding site Glu318, Lys320 and Lys322 etc as well as an EcoRI site at the 5' end and a SacI site at the 3' end for the purpose of gene clone. ScBsAb constructed by this strategy is expected to have the prolonged half life time in vivo and the effect for inducing CDC similar to Fc. (2) HSA interlinker: Because of the smaller size, small molecular antibodies have fast renal clearance, which results in a short retention time in immunotherapy thus causing curative effects unperfect although the shorter half life time is benefit for immunoimaging diagnosis of tumors. Therefore, we devised HSA interlinker which is expected to prolong the half life time of ScBsAb in vivo, improve the stability and solubility of ScBsAb. HSA (human serum album) is an important component of human serum. It is widely used as a stable natural vector because of its stability, several week half-life time, lack of specific enzymatic and immunological activities and slow clearance in liver. It was showed in research that the stability of proteins fused with HSA increased 20 to 40 times in animals. HSA molecule with 585 amino acids in length is composed of three domains, wherein the third domain DIII alone possesses the vector function of the whole molecule. Herein, a fragment with 25 residues from 403 to 427 of DIII domain, which is lack of Cys but rich in polar amino acids in HSA was used as another interlinker in construction of BsAb to improve the stability and prolong the half-life time in vivo. (3) 205c' interlinker: This interlinker is 25 amino acids in length devised by Gruber in construction of anti-TCRxanti-fluorescence scBsAb. The purpose of utilizing 205c' interlinker was to compare and verify the efficacy of interlinkers designed in the present invention and the value of the said design in construction of anti-ovarian BsAb.

Facing HAMA problem induced by murine antibodies in clinic that strongly limits repeated use and dose, further causing the poor curative efficacy, murine antibodies must be humanized to minimize their heterology, which is the urgent affairs for preparation of antibodies used in clinic. The scFv against CD3 molecule in ScBsAb used in the present invention is a reshaped antibody through humanization. The reshaped antibody, so-called CDR-grafted antibody or humanized antibody, is constructed by grafting complementarity-determining regions (CDRs) from the variable domains of rodent antibodies into the framework regions of human variable domains. The space structure of antigen-binding sites of antibodies is mainly determined by six CDRs of variable domains. The said CDRs form three loops, which have decisive effects in antigen-antibody recognition, in the upper site of variable domains supported by four β-sheet domains. The said reshaped antibody remains the antigen-binding ability as well as the most characteristics of human antibody, therefore minimizing HAMA response effectively.

Ovarian cancer remains the leading cause of death from gynecologic malignancies. The five-year survival rate maintains only 30%. Because of lack of the effective diagnostic methods for ovarian cancer located deep into pelvic cavity and the vague symptoms associated in the earlier stage, most patients with ovarian cancer present with an advanced stage of cancer. Although methods of surgical operation advance, drugs of chemotherapy renew and treatments of radiotherapy improve stepwise, the prognosis of ovarian cancer didn't improve at all. The easy recurrence after surgical operation and the side effects and drug tolerance after repeated use of chemotherapy strongly influence the effects of treatments. Therefore, specific diagnostic methods for earlier stage of cancer and the timely clearance of residual focuses are the key step for improving prognosis. BsAb against the related antigens of ovarian cells is regarded as powerful tools in clinic.

SUMMARY OF THE INVENTION

The object of the present invention is to provide a biological preparation with low toxicity, high efficiency and cost-effectiveness against ovarian cancers-anti-human ovarian cancer×anti-human CD3 bispecific antibody developed by gene engineering technology.

Another object of the present invention is to provide a nucleotide sequence encoding the said BsAb.

Another object of the present invention is to provide a vector for the said nucleotide sequence.

Further object of the present invention is to provide a host cell transformed by the expression vector used in the invention.

In addition, based on the context of the disclosure, another aspects of the present invention will be apparent to those with skill in the art.

BRIEF DESCRIPTION OF THE DRAWINGS

FIG. 2 shows the nucleotide sequences of variable domains of heavy chain (SEQ ID NO: 1) and light chain (SEQ ID NO: 3) of anti-ovarian monoclonal antibody and the amino acid sequences (SEQ ID NO: 17 and SEQ ID NO: 18 respectively) encoded by the said nucleotide sequences;

FIG. 5 shows the nucleotide sequences of variable domains of heavy chain (SEQ ID NO: 5) and light chain (SEQ ID NO: 7) of anti-CD3 reshaped scFv and the amino acid sequences (SEQ ID NO: 19 and SEQ ID NO: 20 respectively) encoded by the said nucleotide sequences;

FIG. 6 is antigen-binding activity of anti-CD3 reshaped scFv tested by FACS;

FIG. 8 shows the nucleotide sequences of three kinds of interlinkers (Fc interlinker: SEQ ID NO: 22; HSA interlinker: SEQ ID NO: 24: 205C' interlinker: SEQ ID NO: 26) and the amino acid sequences (Fc interlinker: SEQ ID NO: 23; HSA interlinker: SEQ ID NO: 25; 205C' interlinker: SEQ ID NO: 27) encoded by the said nucleotide sequences;

DETAILED DESCRIPTION OF THE INVENTION

Figure 1:
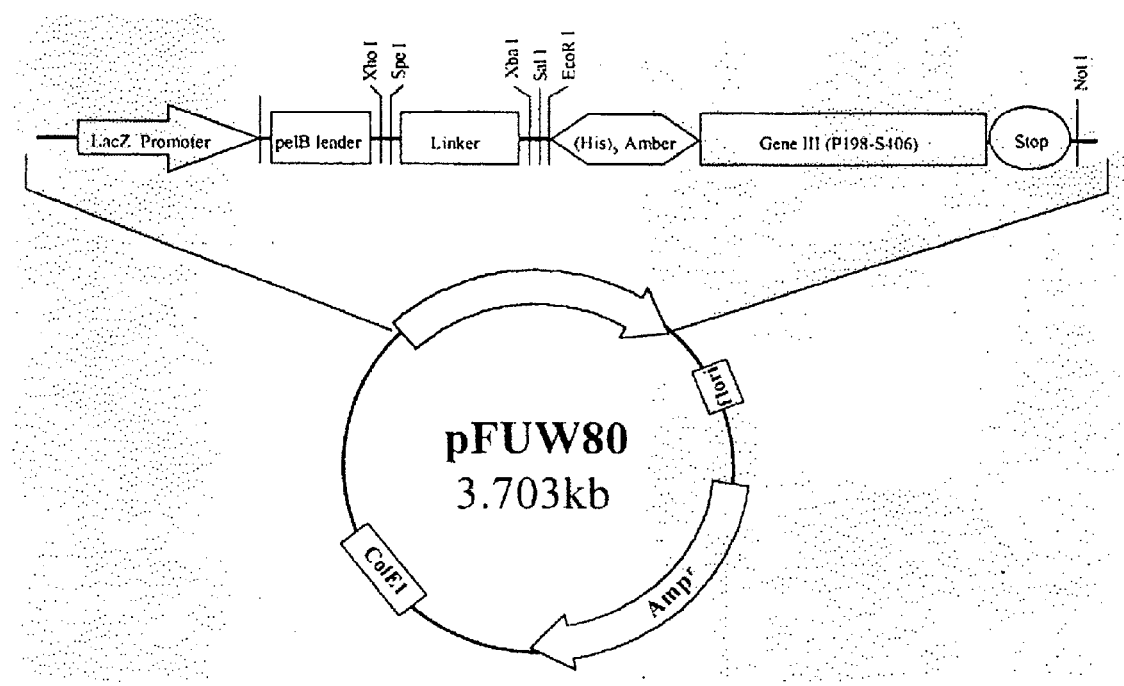
FIG. 1 is a schematic presentation of plasmid pFUW80.
Figure 3:
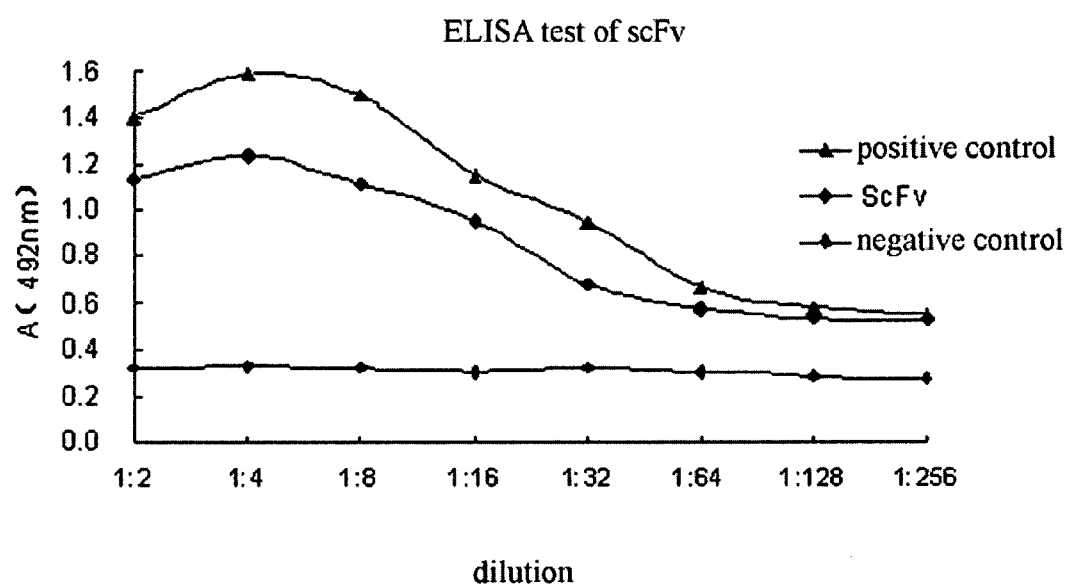
FIG. 3 is activity of anti-ovarian scFv tested by ELISA.

One antibody molecule consists of two identical heavy chains and light chains, each of which is composed of one variable region and one or more constant region. The variable region is responsible for binding with antigens and the constant region is mainly responsible for binding with effect molecules. There are three flexible loops with high variability in each variable region, termed complementarity-determining regions (CDRs), which are mainly responsible for recognizing antigens. The other parts of variable regions, are composed of the rigid β-sheets and support the so-called framework regions (FRs). CDRs and FRs arrange alternatively forming the "Sandwich" structure. In the present invention, the used terms have meanings as follows:

"Fab antibody" refers to a heterodimer formed by Fd fragment (consisting of heavy chain $V_H$ and CH1) and the whole light chain which is connected to the former by a interchain disulfide. The size of "Fab antibody" is ⅓ of the whole antibody and it contains only one antigen binding site.

"Single chain antibody (scFv)" refers to an antibody fragment constructed by gene engineering and a recombinant protein consisting of heavy chain variable region ($V_H$) and light chain variable region ($V_L$) which is joined to the former by a linker. The size of scFv is about ⅙ of the whole antibody.

"Single domain antibody" consists of the heavy chain variable region ($V_H$) or the light chain variable region ($V_L$). Since this antibody fragment consists of only one domain, it is called single domain antibody. The size of this fragment is 1/12 of the whole antibody.

"Minimal recognizing unit (MRU)" consists of single CDR and its size is about 1/70 or 1/80 of the whole antibody.

"Reshaping antibody" is also called "CDR-grafted antibody". Using gene synthesis or site-directed mutation, CDRs in human antibody are replaced by those from murine antibody, therefore the antigen-binding specificity of murine antibody was kept. However, it should be considered that some amino acid residues in human FRs are capable of interfering the conformation of antigen-binding site formed by murine CDRs. Therefore, individual amino acid residues in FRs need be mutated to obtain antibodies humanized to the most extent and with high affinity.

The present invention provides a genetically engineered bispecific antibody against ovarian cancers, wherein the antibody is the whole antibody molecule, Fab, single domain antibody or single-chain Fv (ScFv).

Preferably, the genetically engineered bispecific antibody against ovarian cancer consists of two different single-chain antibodies.

In the present invention, the genetically engineered bispecific antibody against ovarian cancers is preferably a hybrid protein consisting of the single-chain Fv against ovarian cancer and the reshaped single-chain Fv against human CD3. The said proteins is the expressed products, which are capable of activating T lymphocytes to kill ovarian cancer cells specifically, of anti-ovarian scFv and anti-CD3 reshaped scFv connected by three interlinkers.

In bispecific antibodies of the present invention, the said anti-ovarian scFv can contain the amino acid sequence of heavy chain variable domain as follows:

1  Glu Val Gln Leu Gln Glu Ser Gly Pro Glu

11  Val Lys Lys Pro Gly Glu Thr Val Arg Ile

-continued

```
 21   Ser Cys Lys Ala Ser Gly Tyr Thr Phe Thr

31   Thr Ala Gly Met Gln Trp Val Gln Lys Met

41   Pro Gly Lys Gly Leu Lys Trp Leu Gly Trp

51   Ile Asn Thr Asn Ser Glu Val Pro Lys Tyr

61   Ala Glu Asp Phe Arg Gly Arg Phe Ala Phe

71   Ser Leu Glu Thr Ser Ala Ser Thr Ala Tyr

81   Leu Gln Ile Ser Asn Leu Lys Asn Glu Asp

91   Thr Ala Thr Phe Phe Cys Ala Arg Ser Phe

101   Thr Trp Gly Thr Met Asp Tyr Trp Gly Gln

111   Gly Thr Thr Val Thr Val Ser Ser
```

In bispecific antibodies of the present invention, the said anti-ovarian scFv can contain the amino acid sequence of light chain variable domain as follows:

```
  1   Asp Val Val Met Thr Gln Thr Pro Leu Ser

11   Leu Pro Val Ser Leu Gly Asp Gln Ala Ser

21   Ile Ser Cys Arg Ser Ser Gln Thr Leu Val

31   His Ser Ile Gly Asn Thr Tyr Leu His Trp

41   Tyr Leu Gln Lys Pro Gly Gln Ser Pro Lys

51   Leu Leu Ile Tyr Lys Val Ser Asn Arg Phe

61   Ser Gly Val Pro Asp Arg Phe Ser Gly Ser

71   Gly Ser Gly Thr Asp Phe Thr Leu Lys Ile

81   Ser Arg Val Glu Ala Glu Asp Leu Gly Val

91   Tyr Phe Cys Ser Gln Ser Thr His Val Pro

101   Tyr Thr Phe Gly Gly Gly Thr Lys Leu Glu

111   Leu Lys
```

In bispecific antibodies of the present invention, the said anti-human CD3 reshaped scFv can contain the amino acid sequence of heavy chain variable domain as follows:

```
  1   Gln Val Gln Leu Val Gln Ser Gly Ala Glu

11   Val Arg Lys Pro Gly Ala Ser Val Arg Val

21   Ser Cys Lys Ala Ser Gly Tyr Thr Phe Thr

31   Arg Tyr Thr Met His Trp Val Arg Gln Ala

41   Pro Gly His Gly Leu Glu Trp Ile Gly Tyr

51   Ile Asn Pro Ser Arg Gly Tyr Thr Asn Tyr

61   Asn Gln Lys Phe Lys Asp Arg Val Thr Met

71   Thr Thr Asp Lys Ser Phe Ser Thr Ala Ile

81   Met Asp Leu Arg Ser Leu Arg Ser Asp Asp

91   Ser Ala Val Tyr Tyr Cys Ala Arg Tyr Tyr

101   Asp Asp His Tyr Cys Leu Asp Tyr Trp Gly

111   Gln Gly Thr Thr Val Thr Val Ser Ser
```

In bispecific antibodies of the present invention, the said anti-human CD3 reshaped scFv can contain the amino acid sequence of light chain variable domain as follows:

```
  1   Glu Ile Val Leu Thr Gln Ser Pro Ala Thr

11   Leu Ser Leu Ser Pro Gly Glu Arg Ala Thr

21   Leu Ser Cys Ser Ala Ser Ser Ser Val Ser

31   Tyr Met Asn Trp Tyr Gln Gln Lys Pro Gly

41   Gln Ala Pro Arg Arg Trp Ile Tyr Asp Thr

51   Ser Lys Leu Ala Ser Gly Ile Pro Ala Arg

61   Phe Ser Gly Ser Gly Ser Gly Thr Asp Phe

71   Thr Leu Thr Ile Ser Ser Leu Glu Pro Glu

81   Asp Phe Ala Thr Tyr Tyr Cys Gln Gln Trp

91   Ser Ser Asn Pro Phe Thr Phe Gly Gly Gly

101   Thr Lys Val Glu Ile Lys Arg
```

In bispecific antibodies of the present invention, the interlinker connecting two single-chain Fv antibodies can contain the amino acid sequence as follows:

```
  1   Asn Ser Thr Tyr Arg Val Val Ser Val Leu

11   Thr Val Leu His Gln Asp Trp Leu Asn Gly

21   Lys Glu Tyr Lys Cys Lys
```

In bispecific antibodies of the present invention, the interlinker connecting two single-chain Fv antibodies can contain the amino acid sequence as follows:

```
  1   Phe Gln Asn Ala Leu Leu Val Arg Tyr Thr

11   Lys Lys Val Pro Gln Val Ser Thr Pro Thr

21   Leu Val Glu Val Ser
```

In bispecific antibodies of the present invention, the interlinker connecting two single-chain Fv antibodies can contain the amino acid sequence as follows:

```
  1   Ala Ser Ala Asp Asp Ala Lys Lys Asp Ala

11   Ala Lys Lys Asp Asp Ala Lys Lys Asp Asp

21   Ala Lys Lys Asp Leu
```

The present invention still provides a nucleotide sequence encoding the said BsAb, herein containing the nucleotide sequences of two scFvs and the interlinkers between two scFvs. The said interlinker may be any kind of which are capable of ensuring the proper folding of each of two antibodies, furthermore keeping the biological activities of the said antibodies. In addition, the said interlinker should endow BsAb some novel properties to the products. Fc interlinker and HSA interlinker designed and constructed in the present invention and 205c' interlinker cited in the present invention are preferred.

The present invention provides the universal *E. coli* plasmids for construction and expression of BsAb and the expression plasmids containing the nucleotide sequences encoding BsAb of the present invention. In the preferred embodiment of the present invention, one plasmid is pALM derived from plasmid pAL781, which is a universal plasmid for expression of BsAb. The said plasmid has characteristics as follows: Based on the constructed BsAb, different types of BsAbs can be generated by replacing anyone kind of scFv genes. The plasmid from pALM containing the nucleotide sequences encoding BsAb of the present invention was named pALMB. Another plasmid is pETAE, a derivative of pET16 by inactivating EcoRI site, contains lac operator and T7 promoter, which makes pETAE an vector for expression of target proteins with efficiency. The plasmid from pETAE containing the nucleotide sequences encoding BsAb of the present invention was named pEMAB. Another plasmid is pTMF, which was constructed from pET28a according to the restriction endonuclease sites of BsAb and for the sake of the need of further research and is a plasmid for expression of proteins not limited to BsAb with high efficiency. Besides the high efficiency of expression, the plasmid has the characteristics as follows: it has several rare restriction endonuclease sites to facilitate insertion of various foreign genes in the manner of co- or fusion expression; there is a thrombin site between two groups of restriction endonuclease sites, which facilitates the isolation of the desired protein from the fusion protein; there is six codons encoding six His residue at 3' end of the multiclonig site, which facilitates the purification of expressed products with metal chelating chromatography. The plasmid from pTMF containing the nucleotide sequences encoding BsAb of the present invention was named pTMAB.

The present invention still provides the host cells containing the above described expression vectors. The said host cells are preferably *E. coli*.

The steps for production of genetically engineered BsAbs of the present invention are described as follows:

1. VH and VL genes of the monoclonal antibody were amplified from the hybridoma cell line secreting monoclonal antibody against tumor, respectively, by PCR technology using the designed primers.

2. The obtained VH and VL genes against tumors were inserted into the universal scFv expression plasmid, which was transformed into *E. coli*, induced, expressed and characterized.

3. The amino acid sequences of reshaped VH and VL were designed, respectively, according to the antigen binding sites of mouse anti-human CD3 monoclonal antibody OKT3 by using molecular modeling. The nucleotide acid sequences were deduced with *E. coli* bias codons. The whole genes of VH and VL were obtained by splicing the synthetic oligonucleotide fragments using PCR.

4. The resulting VH and VL genes of reshaped anti-human CD3 antibody were inserted into the universal single-chain antibody expression vector, which was transformed into *E. coli*, expressed under induction and characterized.

5. The plasmid with a strong promoter was selected as the starting plasmid. A DNA fragment containing the restriction endonuclease sites which are not present in the starting plasmid, two scFvs and three interlinkers was designed, synthesized and used to replace the multicloning site of the starting plasmid. The synthesized oligonucleotide sequences of interlinkers are inserted into the corresponding sites in the new multicloning site, respectively. Therefore, the universal intermediate vectors containing the interlinkers for BsAbs were constructed.

6. A pair of primers was designed and scFv gene with flanking suitable digestion sites was amplified by PCR from the plasmid containing anti-CD3 reshaped scFv. The gene fragment was inserted into the intermediate vectors for bispecific antibody to yield anti-human CD3-based universal expression vectors for ScBsAb. The vectors were transformed into *E. coli*, expressed under induction and the effects of different interlinkers on the expression of scFvs were characterized.

7. The gene fragment of anti-human ovarian carcinoma scFv was obtained by digesting the expression vector containing the gene of anti-human ovarian carcinoma scFv with double restriction endonucleases. The expression vector for bispecific antibody was constructed by inserting the said gene fragment into the corresponding restriction sites of anti-human CD3-based universal expression vector for ScBsAb.

8. The said expression vector from 7 was transformed into *E. coli*. BsAb was expressed under induction. The molecular mass, expression amount and expression form were analyzed by SDS-PAGE. The anti-tumor activity of the expressed products was tested by ELISA. The anti-human CD3 activity of the expressed products was tested by FACS. The expressed products mediated anti-tumor capability and specificity was assayed using Jurkat cells or human peripheral blood lymphocytes.

9. The expression vector with high efficiency was constructed and the gene of BsAb was inserted into the said vector, resulting in the expression vector with high efficiency for BsAb.

10. The constructed vector with high efficiency was transformed into the host cells.

11. The transformed host cells were cultured and induced for the expression of the said BsAb.

12. The expressed BsAb was isolated.

In additon, the present invention still relates to the drug compositions for the treatments or prevention of tumors containing anti-human ovarian cancer×anti-human CD3 bispecific antibody and the pharmaceutical vectors of the present invention and uses of anti-human ovarian cancer× anti-human CD3 bispecific antibody in preparation of drugs for the treatments or prevention of tumors and in the treatments or prevention of tumors thereof.

The present invention will now be described further by way of the following examples which are intended to be illustrative only and not limited to the scope of the present invention.

An embodiment is disclosed in following paragraphs.

1. Construction of Anti-Ovarian Carcinoma scFv and Anti-Human CD3 scFv (1) Construction of Anti-Ovarian Carcinoma scFv Antibody VH and VL genes of monoclonal antibody COC183B2 against human ovarian carcinoma were cloned, respectively, by RT-PCR and PCR technology with primers hybridizing to FR1 and FR4 sequences of VH or VL region of mouse immunoglobulin (shown in FIG. 2). VH and VL fragments were cloned to plasmid pUC19 and verified by DNA sequencing. Plasmid pFVB2 was created by inserting VH and VL genes to plasmid pFUW80 (shown in FIG. 1) constructed by our lab with the order of VH and VL from 5' to 3' end and there is a $(Gly_4Ser)_3$ linker (SEQ ID NO: 15) between VH and VL. *E. coli* strain Top10 was used for the propagation of plasmid and the positive plasmid was verified by digestion with proper restriction endonucleases. *E. coli* strain XL1-Blue was transformed with pFVB2 and infected by helper phage M13KO7. The phage particles were rescued and the binding activity of the phage antibody was assayed by indirect ELISA. The results indicate that the binding activity of the antibody is 2.5 times higher than that of the negative control, which demonstrates that anti-ovarian carcinoma scFv antibody was constructed successfully.

(2) Construction of Anti-Human CD3 Reshaped scFv Antibody

Figure 4:
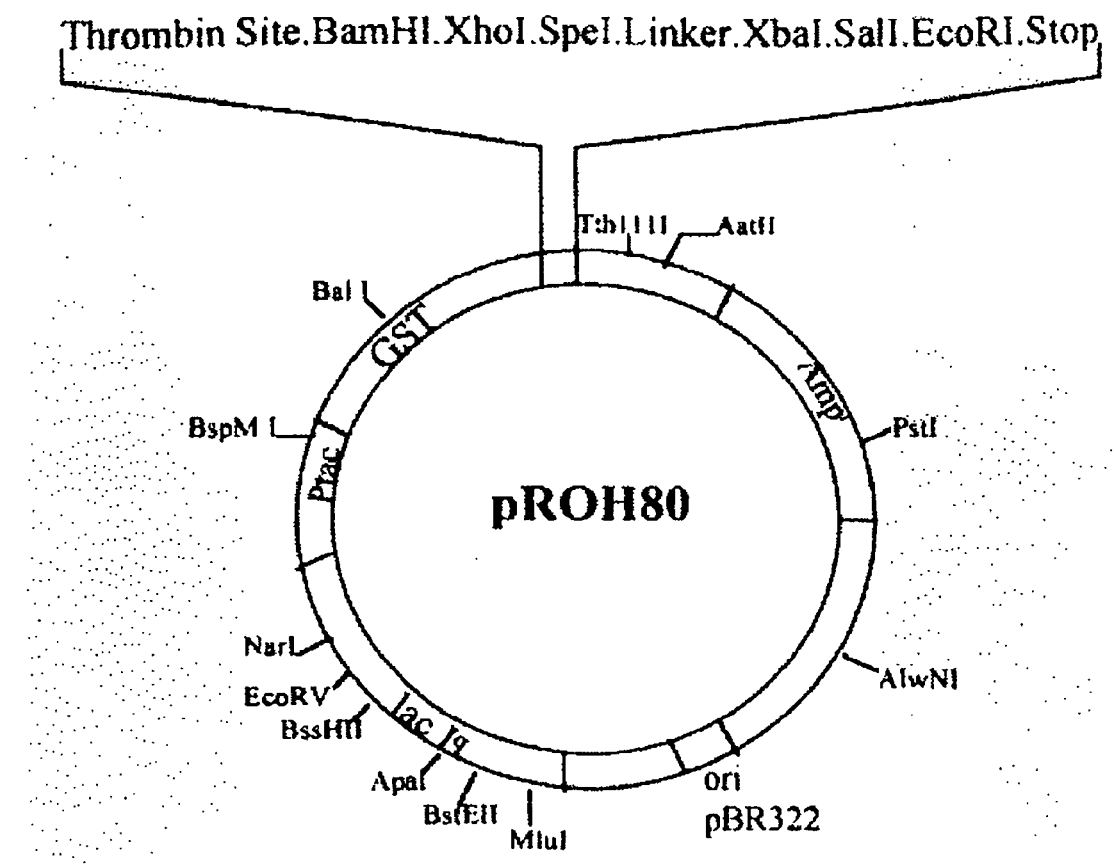
FIG. 4 is a schematic presentation of plasmid pROH80.

The amino acid sequences of reshaped VH and VL were designed, respectively, according to the antigen binding sites of mouse anti-human CD3 monoclonal antibody OKT3 by using molecular modeling. The nucleotide acid sequences were deduced with *E. coli* bias codons. The genes of VH and VL (shown in FIG. 5) were obtained by splicing the synthetic oligonucleotide fragments using PCR. The VH and VL genes of reshaped anti-human CD3 antibody were inserted into the universal single-chain antibody expression vector pROH80 (shown in FIG. 4) in the orientation of VL-(Gly4Ser)3-VH from 5' to 3' end. *E. coli* strain Top10 was used for propagation of the yielding plasmid pROCD3 and the positive plasmids were verified by digestion with proper restriction endonucleases. Single colony was picked up from the transformed Top10 plate and incubated in LB medium with corresponding antibiotics at 37° C. overnight. An aliquot of the culture was transferred to the fresh medium with the proportion of 1-5% and shaking at 37° C. until an OD600 of 0.5-1.0 was reached. IPTG was added to the final concentration of 0.4 mM to induce expression of target proteins. The antigen-binding activity of reshaped anti-CD3 scFv was assayed by FACS. The results demonstrates that the competitive inhibition rate of anti-CD3 reshaped scFv to anti-CD3 monoclonal antibody was 18% (shown in FIG. 6), which implies anti-human CD3 reshaped scFv was constructed and expressed successfully.

Figure 7:
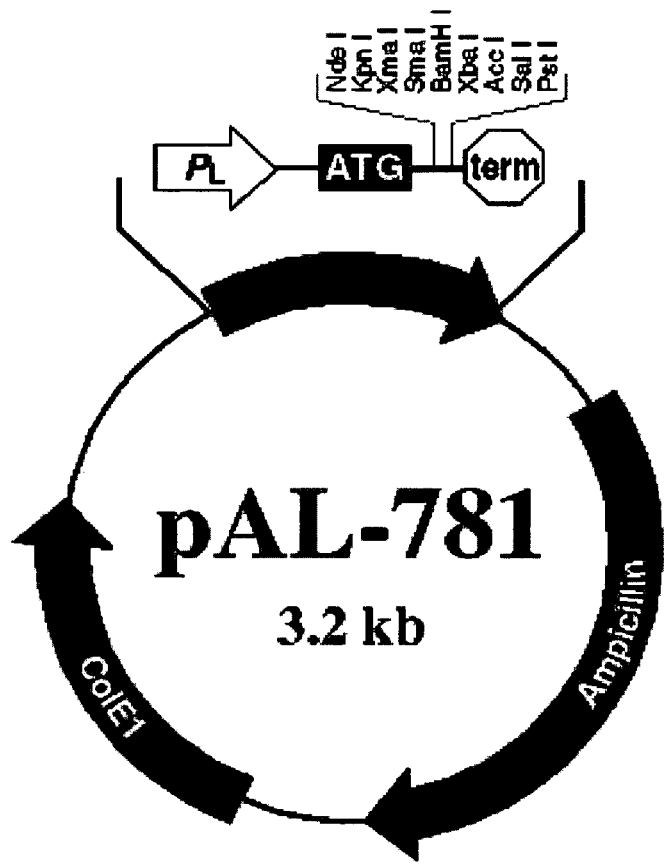
FIG. 7 is a schematic presentation of plasmid pAL781 and the synthesized multi-cloning site (SEQ ID NO: 21 and SEQ ID NO: 28)
Figure 9:
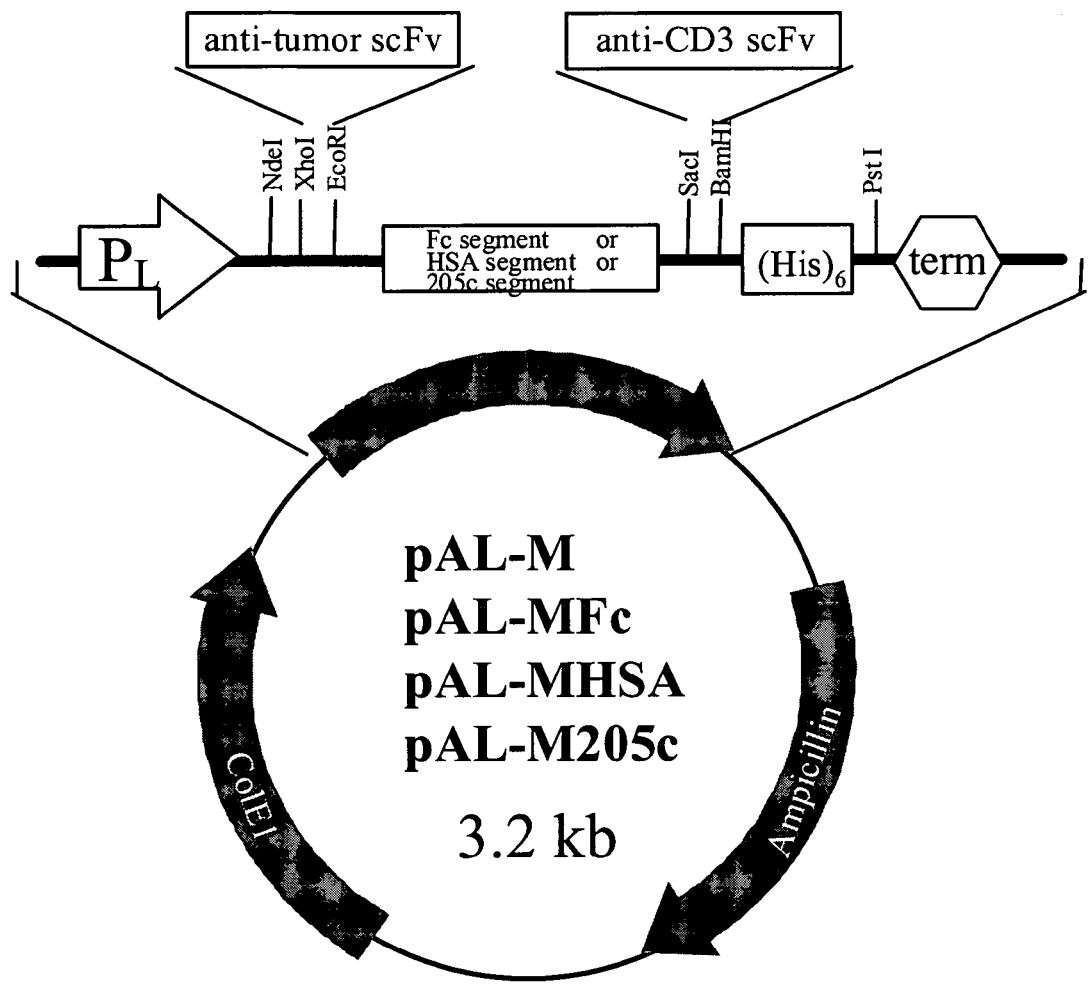
FIG. 9 is a schematic presentation of plasmid palm.

2. Construction and Expression of Anti-Human Ovarian Carcinoma×Anti-Human CD3 Bispecific Antibody (1) Construction of Intermediate Vector for Bispecific Antibody An expression vector with suitable restriction endonuclease sites was constructed for the insertion of two above described scFvs and interlinker. Plasmid pAL-781 (shown in FIG. 7) was chosen as the starting vector to construct the vector for bispecific antibodies. In the present invention, an oligonucleotide fragment with 55 bps was designed and synthesized to replace the multiple clone sites (MCS) in pAL-781. This intermediate vector was named pALM. The new MCS contains the start codon ATG integrated in restriction endonucleases site NdeI. The gene fragment of anti-ovarian carcinoma scFv was inserted between XhoI and EcoRI, interlinker was inserted between EcoRI and SacI and the gene fragment of anti-CD3 reshaped scFv was inserted between SacI and BamHI. And the following was DNA fragment $(CATCAC)_3$ (SEQ ID NO: 16) encoding 6 His and the stop codon TAA. Anyone of the components mentioned above could be substituted for another by digestion and insertion. 3 kinds of the synthetic interlinkers fragments (shown in FIG. 8) were inserted into the proper restriction sites on pALM. Three intermediate vectors for ScBsAb: pALM-Fc; pALM-HSA and pALM-205c' (shown in FIG. 9) were constructed successfully and verified by digestion and DNA sequencing.

(2) Construction of CD3-based Universal Expression Vector for ScBsAb

A pair of primers were designed for amplification of CD3 scFv gene with flanking digestion sites SacI at 5' end and BamHI at 3' end from the plasmid containing anti-CD3 reshaped scFv by PCR. The gene fragment was inserted into the intermediate vector for bispecific antibody to yield anti-human CD3-based universal expression vector for ScBsAb. The resulting vector was transformed to *E. coli* strain GI724 and the protein was expressed. The results indicate that all of three kinds of interlinkers had no negative effects on the expression of scFv.

(3) Construction of Bispecific Antibody

The gene fragment of anti-human ovarian carcinoma scFv was obtained by digesting the expression vector containing the gene of anti-human ovarian carcinoma scFv with restriction endonucleases XhoI and EcoRI. The expression vector for bispecific antibody was constructed by inserting the said gene fragment into anti-human CD3-based universal expression vector for ScBsAb. The resulting plasmids were propagated in *E. coli* strain GI724, verified by digestion with proper restriction endonucleases and named pAMAB.

(4) Expression of Bispecific Antibody in *E. coli*

Single colony of *E. coli* strain GI724 harboring pAMAB was picked up and incubated in RM medium overnight at 30° C. An aliquot of culture was transferred to fresh medium with the proportion of 20%. When an OD550 of the culture was reached 0.5-1.0, tryptophan was added to the final concentration of 100 ug/ml to induce expression of the target protein. After 3 hours of induction, culture was precipitated by centrifugation at 3,000 rpm for 10 min at 4° C. The cell pellet was resuspended in ½ culture-volume of PBS and broken by ultrasonic in ice bath for 20 s for 6-8 times with 1-min interval followed by centrifugation at 4° C. at 12,000 rpm for 20 min. The precipitate was resuspended in PBS with the same volume to the supernatant. The sonicate, supernatant and precipitate of sonication were analyzed by 12% SDS-PAGE with the empty vector pALM as negative control. Protein with molecular weight of 52 kDa was found in both supernatant and precipitate. The result indicated the target protein was expressed partly in soluble form. The soluble protein could be used directly to identify the biological activity of bispecific antibody.

Figure 12:
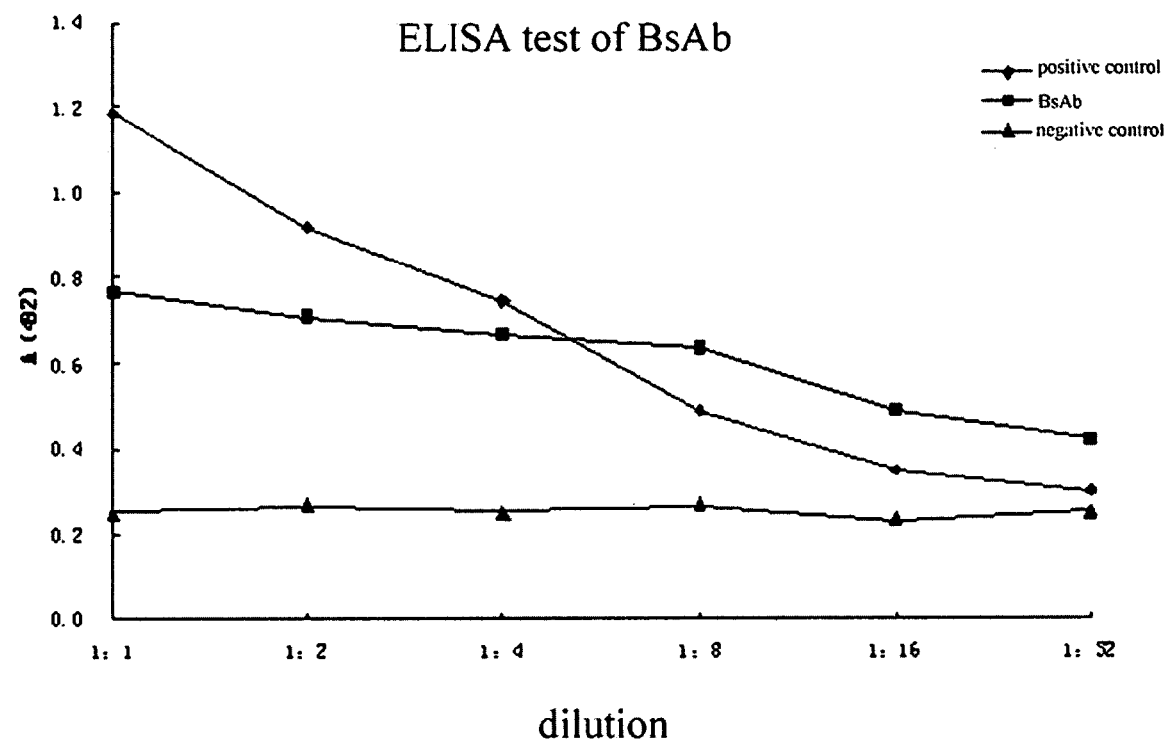
FIG. 12 is anti-ovarian activity of BsAb tested by ELISA.

3. Biological Activity Assay of Anti-Human Ovarian Carcinoma×Anti-Human CD3 Bispecific Antibody (1) Antigen-Binding Activity of Anti-Human Ovarian Carcinoma scFv The antigen-binding activity of anti-ovarian carcinoma scFv in bispecific antibody was assayed by direct ELISA. ELISA plate was coated with bispecific antibody at 4° C. overnight. Wells coated with anti-ovarian monoclonal antibody were set as positive control. Plate was washed 3 times with PBST (PBS-0.05% Tween 20) for 5 min. HRP-OC183B2 diluted in 3% goat serum was added and incubate at 37° C. for 1 h. After washing plate 3 times with PBST, the substrate of HRP was added and incubated for 20 min at room temperature in the dark. 2M H2SO4 was added to stop the reaction. The plates were read at 492 nm (data shown in FIG. 12). All the values of OD492 of bispecific antibody were 2.5 times higher than those of negative control and changed with gradient among the different dilution of bispecific antibody. The data indicates that anti-ovarian scFv in bispecific antibody has the binding activity to antigens associated with ovarian carcinoma.

(2) Antigen-Binding Activity of Anti-Human CD3 scFv

The antigen-binding activity of anti-CD3 reshaped scFv in bispecific antibody was assayed by FACS according to the principle of competitive inhibition. 1×106 fresh Jurkat cells in an FACS tube were washed 3 times with PBS containing 2% fetal bovine serum and 0.1% NaN3. Bispecific antibody was added before the cells were incubated at 4° C. for 45 min. Cells incubated with PBS were set as positive control. After washed 3 times with PBS containing 2% fetal bovine serum and 0.1% NaN3, the cells were incubated with diluted murine anti-CD3 monoclonal antibody for 30 min at 4° C. After washed 3 times with PBS containing 2% fetal bovine serum and 0.1% NaN3, the cells were incubated with goat anti-mouse IgG-FITC (with the dilution of 1:50) for 45 min at 4° C. After washed 2 times with PBS containing 2% fetal bovine serum and 0.1% NaN3, the cells were resuspended in 500 ul PBS and assayed on FACSort. The data indicate bispecific antibody can greatly inhibit the antigen-binding activity of anti-CD3 mouse monoclonal antibody. The inhibition rate is 18%, which demonstrates anti-CD3 reshaped scFv in bispecific antibody has binding activity to CD3. The results indicate two scFvs within bispecific antibody both keep their antigen-binding activities.

(3) Cytotoxicity of Anti-Ovarian Bispecific Antibody Against Ovarian Carcinoma Cells Human ovarian cell line SKOV3 cells (target cells) were seeded in 96-well plate with approximate 1×104/well. Bispecific antibody renatured from inclusion bodies were added at three different volumes of 5 ul, 10 ul and 20 ul. Plates were incubated in the incubator with CO2 overnight. Jurkat cells (effector cells) were added at different effector cells: target cells ratios. Plates were incubated in the incubator with CO2 at 37° C. for 48 h. 25 ul MTT was added to each well. After incubation at 37° C. for 4 h, the plates were emptied and 100 ul acidic SDS (0.1N HCl, 1% SDS) was added to each well. After incubation at 37C overnight, plates were read at 570 nm. The rate of cytotoxicity was calculated according to the formula below.

$$\text{Cytotoxicity \%} = \frac{OD_{E+T} - OD_E}{1 - OD_T} \times 100\%$$

Figure 13:
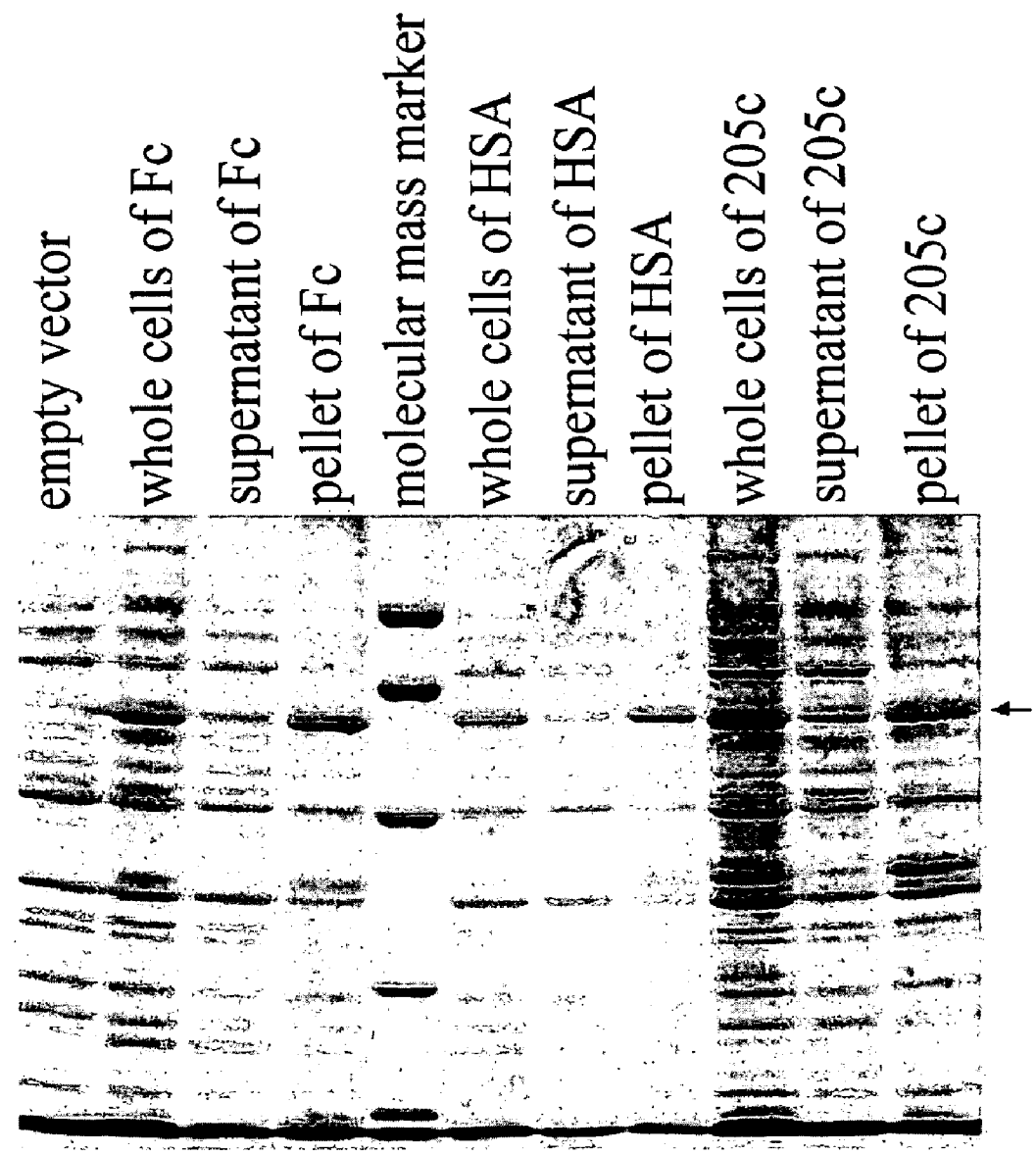
FIG. 13 is SDS-PAGE analysis of bispecific antibody expressed from pTMF.

As shown in Table 1, the cytotoxicity rate of effector cells against target cells increased in the case of addition of bispecific antibody (shown in FIG. 13). The rate cytotoxicity increases with the increase of the concentration of bispecific antibody, which indicates bispecific antibody triggers the direct killing effect of effector cells against target cells.

TABLE 1

| E/T | BsAb 140 µg/ml | | | |
|---|---|---|---|---|
| | 0 µl | 5 µl | 10 µl | 20 µl |
| | cytotoxicity % | | | |
| 12.5:1 | 97.39 | 100.00 | 110.76 | 144.64 |
| 6.2:1 | 69.56 | 55.09 | 113.27 | 104.29 |
| 3.1:1 | 33.48 | 46.30 | 52.02 | 64.38 |

4. Construction of High Performance Expression Vector

Figure 10:
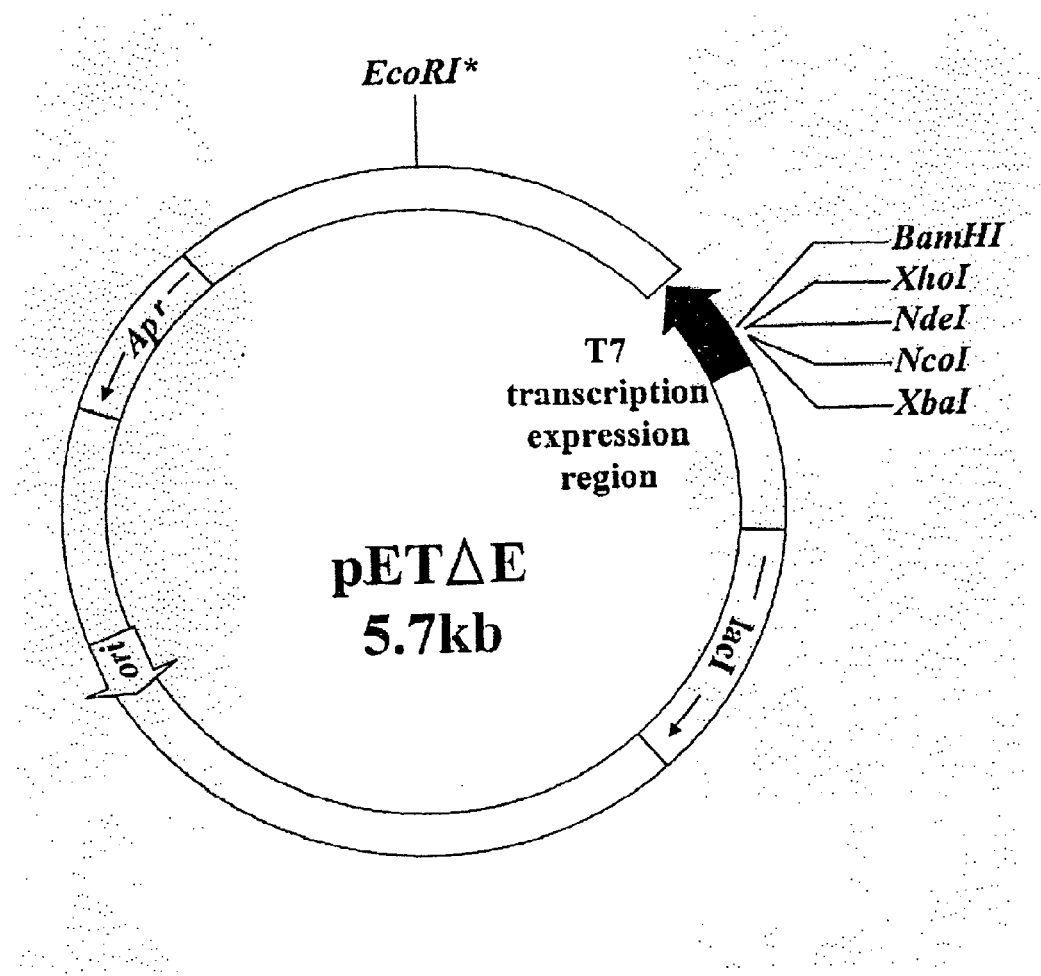
FIG. 10 is a schematic presentation of plasmid pETAE.
Figure 11:
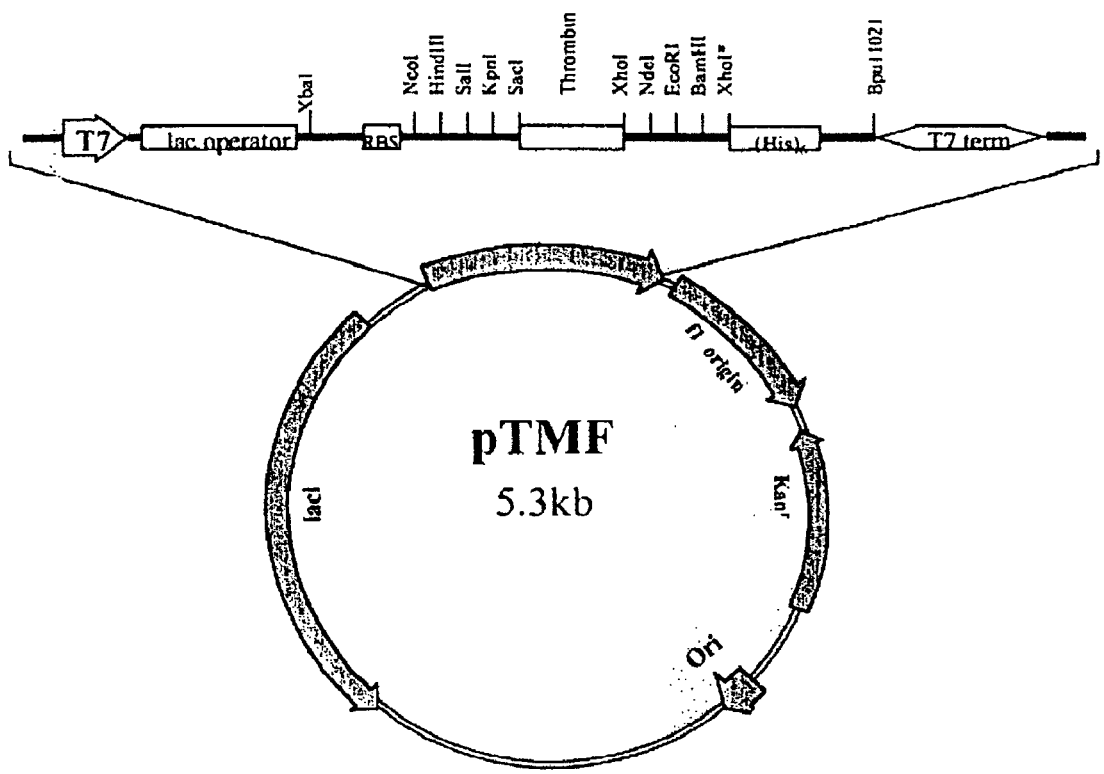
FIG. 11 is a schematic presentation of plasmid pTMF.

For production purpose, high performance expression vector was constructed for overexpression of bispecific antibody. pETΔE (shown in FIG. 10) derived from pET16 by inactivated EcoRI site is a T7 promoter-based high performance expression vector. The bispecific antibody gene fragment digested from pAMAB with XhoI and BamHI was inserted into the same sites of pETAE digested with the same restriction endonucleases, yielding pEMAB. Proteins were expressed after pEMAB was transformed to E. coli strain BL21(DE3). However, expressed from pETAE, the target protein was fused to (His)10 tag which could not be purified by IMAC as effectively as proteins fused to (His)6. Therefore, plasmid pTMF (shown in FIG. 11) derived from pET28a was constructed. pTMF contains T7 promoter for overexpression of target proteins and several unusual restriction sites which were used for facilitating the insertion of foreign genes followed by fusion or co-expression of target proteins. A thrombin site was designed between two groups of restriction sites. Following purification, the target proteins could be separate from the fusion proteins by proteolysis on thrombin site. Flanking 3' end of MCS is the sequence coding for His6 tag which could be used in IMAC.

The gene fragment of bispecific antibody digested from pAMAB with XhoI and BamHI was inserted into pTMF to generate plasmid pTMAB. E. coli strains BL21(DE3) was transformed with pTMAB, single colony was picked and grown until an the value of OD550 reached 0.5. Protein expression was induced by adding IPTG to a final concentration of 0.4 mM. After 3 hours of induction, the culture was precipitated by centrifugation, cell pellets were broken by ultrasonic and the sonicate was analyzed by SDS-PAGE (shown in FIG. 13). In the total whole-cell proteins, 27% is bispecific antibody 16% of which is soluble. The expression level is eligible in production area.

5. Conclusion

Anti-human ovarian carcinoma×anti-human CD3 bispecific antibody can simultaneously bind to both T cells and ovarian carcinoma cells and then activate T cells to kill the ovarian carcinoma cells. This model of bispecific antibody can be used as biological drugs for the treatment of ovarian carcinoma.

What is claimed is:

1. A bispecific antibody against ovarian cancer, comprising (i) an anti-ovarian cancer single chain antibody comprising a heavy chain variable region and a light chain variable region, said heavy chain variable region of said anti-ovarian cancer single chain antibody comprising the amino acid sequence as set forth in SEQ ID NO: 17, and said light chain variable region of said anti-ovarian cancer single chain antibody comprising the amino acid sequence as set forth in SEQ ID NO: 18; (ii) an anti-human CD3 single chain antibody; and (iii) an interlinker connecting said anti-ovarian cancer single chain antibody to said anti-human CD3 single chain antibody.

2. The bispecific antibody of claim 1, wherein said anti-human CD3 single chain antibody is a reshaped antibody.

3. The bispecific antibody of claim 1 or 2, wherein said heavy chain variable region of said anti-ovarian cancer single chain antibody and said light chain variable region of said anti-ovarian cancer single chain antibody is connected by an intralinker comprising the amino acid sequence set forth in SEQ ID NO: 15.

4. The bispecific antibody of claim 1, wherein said anti-human CD3 single chain antibody comprises a heavy chain variable region and a light chain variable region, said heavy chain variable region of said anti-human CD3 single chain antibody comprising the amino acid sequence set forth in SEQ ID NO: 19.

5. The bispecific antibody of claim 1, wherein said anti-human CD3 single chain antibody comprises a heavy chain variable region and a light chain variable region, said light chain variable region of said anti-human CD3 single chain antibody comprising the amino acid sequence set forth in SEQ ID NO: 20.

6. The bispecific antibody of claim 5, wherein said heavy chain variable region of said anti-human CD3 single chain antibody comprises the amino acid sequence set forth in SEQ ID NO: 19.

7. The bispecific antibody of claim 1, 2, or 6 wherein said interlinker comprises the amino acid sequence set forth in SEQ ID NO; 23.

8. The bispecific antibody of claim 1, 2, or 6, wherein said interlinker comprises the amino acid sequence set forth in SEQ ID NO: 25.

9. The bispecific antibody of claim 1, 2, or 6, wherein said interlinker comprises the amino acid sequence set forth in SEQ ID NO: 27.

10. The bispecific antibody of claim 6 wherein said heavy chain variable region of said anti-ovarian cancer single chain antibody and said light chain variable region of said anti-ovarian cancer single chain antibody is connected by an intralinker comprising the amino acid sequence set forth in SEQ ID NO: 15.

11. The bispecific antibody of claim 10, wherein said interlinker comprises the amino acid sequence set forth in SEQ ID NO: 23.

12. The bispecific antibody of claim 10, wherein said interlinker comprises the amino acid sequence set forth in SEQ ID NO: 25.

13. The bispecific antibody of claim 10, wherein said interlinker comprises the amino acid sequence set forth in SEQ ID NO: 27.

14. The bispecific antibody of claim 10, wherein said bispecific antibody further comprises a segment of six consecutive histidine residues.

15. The bispecific antibody of claim 12, wherein said bispecific antibody further comprises a segment of six consecutive histidine residues.

* * * * *

SEQUENCE LISTING

```
<160> NUMBER OF SEQ ID NOS: 14

<210> SEQ ID NO 1
<211> LENGTH: 354
<212> TYPE: DNA
<213> ORGANISM: Artificial
<220> FEATURE:
<223> OTHER INFORMATION: anti-ovarian scFv amino acid sequence of heavy
      chain variable domain

<400> SEQUENCE: 1
gaggtgcagc tgcaggagtc tggacctgag gtgaagaagc tggagagac  agtcaggatc        60 tcctgcaagg cttctgggta taccttcaca actgctggaa tgcagtgggt gcaaaagatg       120
ccaggaaagg gtttgaagtg gcttggctgg ataaacacca actctgaagt tccaaaatat       180
gcagaagact tcaggggacg gtttgccttc tctttggaga cctctgccag cactgcatat       240
```
ttacagataa gcaacctcaa aaatgaggac acggctacgt ttttctgtgc gagatctttt    300
acttggggga ctatggacta ttgggggcaa gggaccacgg tcaccgtctc ctca    354

<210> SEQ ID NO 2
<211> LENGTH: 354
<212> TYPE: PRT
<213> ORGANISM: Artificial
<220> FEATURE:
<223> OTHER INFORMATION: AA Seq of VH against human ovarian cancer

<400> SEQUENCE: 2

Gly Ala Gly Gly Thr Gly Cys Ala Gly Cys Thr Gly Cys Ala Gly Gly
1               5                   10                  15

Ala Gly Thr Cys Thr Gly Gly Ala Cys Cys Thr Gly Ala Gly Gly Thr
            20                  25                  30

Gly Ala Ala Gly Ala Ala Gly Cys Cys Thr Gly Gly Ala Gly Ala Gly
        35                  40                  45

Ala Cys Ala Gly Thr Cys Ala Gly Gly Ala Thr Cys Thr Cys Cys Thr
    50                  55                  60

Gly Cys Ala Ala Gly Gly Cys Thr Thr Cys Thr Gly Gly Gly Thr Ala
65                  70                  75                  80

Thr Ala Cys Cys Thr Thr Cys Ala Cys Ala Ala Cys Thr Gly Cys Thr
                85                  90                  95

Gly Gly Ala Ala Thr Gly Cys Ala Gly Thr Gly Gly Gly Thr Gly Cys
            100                 105                 110

Ala Ala Ala Ala Gly Ala Thr Gly Cys Cys Ala Gly Gly Ala Ala Ala
        115                 120                 125

Gly Gly Gly Thr Thr Thr Gly Ala Ala Gly Thr Gly Gly Cys Thr Thr
    130                 135                 140

Gly Gly Cys Thr Gly Gly Ala Thr Ala Ala Cys Ala Cys Cys Thr Ala
145                 150                 155                 160

Ala Cys Thr Cys Thr Gly Ala Ala Gly Thr Cys Cys Ala Ala Ala
                165                 170                 175

Ala Thr Ala Thr Gly Cys Ala Gly Ala Ala Gly Ala Cys Thr Thr Cys
        180                 185                 190

Ala Gly Gly Gly Ala Cys Gly Thr Thr Thr Gly Cys Cys Thr
    195                 200                 205

Thr Cys Thr Cys Thr Thr Gly Gly Ala Gly Ala Cys Cys Thr Cys
        210                 215                 220

Thr Gly Cys Cys Ala Gly Cys Ala Cys Thr Gly Cys Ala Thr Ala Thr
225                 230                 235                 240

Thr Thr Ala Cys Ala Gly Ala Thr Ala Ala Gly Cys Ala Ala Cys Cys
                245                 250                 255

Thr Cys Ala Ala Ala Ala Thr Gly Ala Gly Gly Ala Cys Ala Cys
        260                 265                 270

Gly Gly Cys Thr Ala Cys Gly Thr Thr Thr Thr Cys Thr Gly Thr
    275                 280                 285

Gly Cys Gly Ala Gly Ala Thr Cys Thr Thr Thr Thr Ala Cys Thr Thr
        290                 295                 300

Gly Gly Gly Gly Gly Ala Cys Thr Ala Thr Gly Gly Ala Cys Thr Ala
305                 310                 315                 320

Thr Thr Gly Gly Gly Gly Gly Cys Ala Ala Gly Gly Gly Ala Cys Cys
                325                 330                 335

Ala Cys Gly Gly Thr Cys Ala Cys Cys Gly Thr Cys Thr Cys Cys Thr
        340                 345                 350

Cys Ala

<210> SEQ ID NO 3
<211> LENGTH: 336
<212> TYPE: DNA
<213> ORGANISM: Artificial
<220> FEATURE:
<223> OTHER INFORMATION: Anti-ovarian scFv sequence of light chain
      variable domain

<400> SEQUENCE: 3

```
gatgttgtga tgacccaaac tccactctcc ctgcctgtca gtcttggaga tcaagcctcc    60
atctcttgca gatctagtca gacccttgta cacagtattg gaaacaccta tttacattgg   120
tacctgcaga agccaggcca gtctccaaaa ctcctgatct acaaggtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttccg   300
tacacgttcg gagggggac caagctggag ctcaaa                              336
```

<210> SEQ ID NO 4
<211> LENGTH: 336
<212> TYPE: PRT
<213> ORGANISM: Artificial
<220> FEATURE:
<223> OTHER INFORMATION: AA sequence anti-ovarian scFv of light chain
      variable domain

<400> SEQUENCE: 4

```
Gly Ala Thr Gly Thr Thr Gly Thr Gly Ala Thr Gly Ala Cys Cys Cys
1               5                   10                  15
Ala Ala Ala Cys Thr Cys Cys Ala Cys Thr Cys Thr Cys Cys Cys Thr
                20                  25                  30
Gly Cys Cys Thr Gly Thr Cys Ala Gly Thr Cys Thr Thr Gly Gly Ala
            35                  40                  45
Gly Ala Thr Cys Ala Ala Gly Cys Cys Thr Cys Cys Ala Thr Cys Thr
        50                  55                  60
Cys Thr Thr Gly Cys Ala Gly Ala Thr Cys Thr Ala Gly Thr Cys Ala
65                  70                  75                  80
Gly Ala Cys Cys Cys Thr Thr Gly Thr Ala Cys Ala Cys Ala Gly Thr
                85                  90                  95
Ala Thr Thr Gly Gly Ala Ala Ala Cys Ala Cys Cys Thr Ala Thr Thr
            100                 105                 110
Thr Ala Cys Ala Thr Thr Gly Gly Thr Ala Cys Cys Thr Gly Cys Ala
        115                 120                 125
Gly Ala Ala Gly Cys Cys Ala Gly Gly Cys Cys Ala Gly Thr Cys Thr
    130                 135                 140
Cys Cys Ala Ala Ala Ala Cys Thr Cys Cys Thr Gly Ala Thr Cys Thr
145                 150                 155                 160
Ala Cys Ala Ala Gly Gly Thr Thr Thr Cys Cys Ala Ala Cys Cys Gly
                165                 170                 175
Ala Thr Thr Thr Thr Cys Thr Gly Gly Gly Thr Cys Cys Cys Ala
            180                 185                 190
Gly Ala Cys Ala Gly Gly Thr Thr Cys Ala Gly Thr Gly Gly Cys Ala
    195                 200                 205
Gly Thr Gly Gly Ala Thr Cys Ala Gly Gly Gly Ala Cys Ala Gly Ala
    210                 215                 220
```

-continued

```
Thr Thr Thr Cys Ala Cys Ala Cys Thr Cys Ala Ala Gly Ala Thr Cys
225                 230                 235                 240

Ala Gly Cys Ala Gly Ala Gly Thr Gly Gly Ala Gly Gly Cys Thr Gly
                245                 250                 255

Ala Gly Gly Ala Thr Cys Thr Gly Gly Gly Ala Gly Thr Thr Thr Ala
            260                 265                 270

Thr Thr Thr Cys Thr Gly Cys Thr Cys Thr Cys Ala Ala Ala Gly Thr
        275                 280                 285

Ala Cys Ala Cys Ala Thr Gly Thr Thr Cys Cys Gly Thr Ala Cys Ala
    290                 295                 300

Cys Gly Thr Thr Cys Gly Gly Ala Gly Gly Gly Gly Gly Gly Ala Cys
305                 310                 315                 320

Cys Ala Ala Gly Cys Thr Gly Gly Ala Gly Cys Thr Cys Ala Ala Ala
                325                 330                 335

<210> SEQ ID NO 5
<211> LENGTH: 357
<212> TYPE: DNA
<213> ORGANISM: Artificial
<220> FEATURE:
<223> OTHER INFORMATION: Anti-human CD3 reshaped scFv seq of heavy chain
      variable domain

<400> SEQUENCE: 5
caggttcagt tggtgcagtc tggcgctgag gtgaggaagc ctggggcatc agtgagggtc      60
tcctgcaagg cttctggata caccttcacc cgttacacta tgcactgggt gcgtcaggcc     120
cctgggcacg ggcttgagtg gattggatac attaaccctt ccagagggta cactaactac     180
aaccaaaaat tcaaagatag agtgaccatg accactgaca aatccttcag tacagccatc     240
atggacctga gaagtctgag atctgacgac tcggccgtgt actactgtgc tagatactac     300
gacgaccact actgcttgga ttactggggt caaggaacca cggtcaccgt ctcctca        357

<210> SEQ ID NO 6
<211> LENGTH: 357
<212> TYPE: PRT
<213> ORGANISM: Artificial
<220> FEATURE:
<223> OTHER INFORMATION: anti-human CD3 reshaped scFv amino acid
      sequence of heavy chain variable domain

<400> SEQUENCE: 6

Cys Ala Gly Gly Thr Thr Cys Ala Gly Thr Thr Gly Gly Thr Gly Cys
1               5                   10                  15

Ala Gly Thr Cys Thr Gly Gly Cys Gly Cys Thr Gly Ala Gly Gly Thr
            20                  25                  30

Gly Ala Gly Gly Ala Ala Gly Cys Cys Thr Gly Gly Gly Gly Cys Ala
        35                  40                  45

Thr Cys Ala Gly Thr Gly Ala Gly Gly Gly Thr Cys Thr Cys Cys Thr
    50                  55                  60

Gly Cys Ala Ala Gly Gly Cys Thr Thr Cys Thr Gly Gly Ala Thr Ala
65                  70                  75                  80

Cys Ala Cys Cys Thr Thr Cys Ala Cys Cys Cys Gly Thr Thr Ala Cys
                85                  90                  95

Ala Cys Thr Ala Thr Gly Cys Ala Cys Thr Gly Gly Gly Thr Gly Cys
            100                 105                 110

Gly Thr Cys Ala Gly Gly Cys Cys Cys Cys Thr Gly Gly Gly Cys Ala
        115                 120                 125
```

-continued

```
Cys Gly Gly Gly Cys Thr Thr Gly Ala Gly Thr Gly Gly Ala Thr Thr
    130                 135                 140

Gly Gly Ala Thr Ala Cys Ala Thr Thr Ala Ala Cys Cys Cys Thr Thr
145                 150                 155                 160

Cys Cys Ala Gly Ala Gly Gly Gly Thr Ala Cys Ala Cys Thr Ala Ala
                165                 170                 175

Cys Thr Ala Cys Ala Ala Cys Cys Ala Ala Ala Ala Ala Thr Thr Cys
            180                 185                 190

Ala Ala Ala Gly Ala Thr Ala Gly Ala Gly Thr Gly Ala Cys Cys Ala
        195                 200                 205

Thr Gly Ala Cys Cys Ala Cys Thr Gly Ala Cys Ala Ala Ala Thr Cys
    210                 215                 220

Cys Thr Thr Cys Ala Gly Thr Ala Cys Ala Gly Cys Cys Ala Thr Cys
225                 230                 235                 240

Ala Thr Gly Gly Ala Cys Cys Thr Gly Ala Gly Ala Ala Gly Thr Cys
                245                 250                 255

Thr Gly Ala Gly Ala Thr Cys Thr Gly Ala Cys Gly Ala Cys Thr Cys
            260                 265                 270

Gly Gly Cys Cys Gly Thr Gly Thr Ala Cys Thr Ala Cys Thr Gly Thr
        275                 280                 285

Gly Cys Thr Ala Gly Ala Thr Ala Cys Thr Ala Cys Gly Ala Cys Gly
    290                 295                 300

Ala Cys Cys Ala Cys Thr Ala Cys Thr Gly Cys Thr Thr Gly Gly Ala
305                 310                 315                 320

Thr Thr Ala Cys Thr Gly Gly Gly Gly Thr Cys Ala Ala Gly Gly Ala
                325                 330                 335

Ala Cys Cys Ala Cys Gly Gly Thr Cys Ala Cys Cys Gly Thr Cys Thr
            340                 345                 350

Cys Cys Thr Cys Ala
        355
```

<210> SEQ ID NO 7
<211> LENGTH: 321
<212> TYPE: DNA
<213> ORGANISM: Artificial
<220> FEATURE:
<223> OTHER INFORMATION: ant-human CD3 reshaped scFv sequence of light chain variable domain

<400> SEQUENCE: 7

```
gagatcgtac tgacccagtc tccagccacc ctgtctttgt ctccagggga aagagccacc     60
ctctcctgct ccgcatcttc ctccgtttcc tacatgaact ggtaccaaca gaaacctggt    120
caagctccta gaagatggat ctatgacacc tccaaactag caagtggtat cccagctagg    180
ttcagtggca gtggatcagg aacagatttc actctcacca tcagtagcct agagcctgaa    240
gattttgcga cttattattg tcagcaatgg tcttccaacc cgttcacctt cggcggaggg    300
actaaagtgg agatcaaacg a                                              321
```

<210> SEQ ID NO 8
<211> LENGTH: 321
<212> TYPE: PRT
<213> ORGANISM: Artificial
<220> FEATURE:
<223> OTHER INFORMATION: AA Seq ant-human CD3 reshaped scFv light chain variable domain

<400> SEQUENCE: 8

-continued

```
Gly Ala Gly Ala Thr Cys Gly Thr Ala Cys Thr Gly Ala Cys Cys Cys
1               5                   10                  15
Ala Gly Thr Cys Thr Cys Cys Ala Gly Cys Cys Ala Cys Cys Cys Thr
                20                  25                  30
Gly Thr Cys Thr Thr Thr Gly Thr Cys Thr Cys Cys Ala Gly Gly Gly
                35                  40                  45
Gly Ala Ala Ala Gly Ala Gly Cys Cys Ala Cys Cys Thr Cys Thr
50                  55                  60
Cys Cys Thr Gly Cys Thr Cys Cys Gly Cys Ala Thr Cys Thr Thr Cys
65                  70                  75                  80
Cys Thr Cys Cys Gly Thr Thr Thr Cys Cys Thr Ala Cys Ala Thr Gly
                85                  90                  95
Ala Ala Cys Thr Gly Gly Thr Ala Cys Cys Ala Ala Cys Ala Gly Ala
                100                 105                 110
Ala Ala Cys Cys Thr Gly Gly Thr Cys Ala Ala Gly Cys Thr Cys Cys
                115                 120                 125
Thr Ala Gly Ala Ala Gly Ala Thr Gly Gly Ala Thr Cys Thr Ala Thr
                130                 135                 140
Gly Ala Cys Ala Cys Cys Thr Cys Cys Ala Ala Ala Cys Thr Ala Gly
145                 150                 155                 160
Cys Ala Ala Gly Thr Gly Gly Thr Ala Thr Cys Cys Ala Gly Cys
                165                 170                 175
Thr Ala Gly Gly Thr Thr Cys Ala Gly Thr Gly Gly Cys Ala Gly Thr
                180                 185                 190
Gly Gly Ala Thr Cys Ala Gly Gly Ala Ala Cys Ala Gly Ala Thr Thr
                195                 200                 205
Thr Cys Ala Cys Thr Cys Thr Cys Ala Cys Cys Ala Thr Cys Ala Gly
                210                 215                 220
Thr Ala Gly Cys Cys Thr Ala Gly Ala Gly Cys Cys Thr Gly Ala Ala
225                 230                 235                 240
Gly Ala Thr Thr Thr Thr Gly Cys Gly Ala Cys Thr Thr Ala Thr Thr
                245                 250                 255
Ala Thr Thr Gly Thr Cys Ala Gly Cys Ala Ala Thr Gly Gly Thr Cys
                260                 265                 270
Thr Thr Cys Cys Ala Ala Cys Cys Cys Gly Thr Thr Cys Ala Cys Cys
                275                 280                 285
Thr Thr Cys Gly Gly Cys Gly Gly Ala Gly Gly Gly Ala Cys Thr Ala
                290                 295                 300
Ala Ala Gly Thr Gly Gly Ala Gly Ala Thr Cys Ala Ala Ala Cys Gly
305                 310                 315                 320
Ala
```

<210> SEQ ID NO 9
<211> LENGTH: 75
<212> TYPE: DNA
<213> ORGANISM: Artificial
<220> FEATURE:
<223> OTHER INFORMATION: Nuc Seq interlinker connecting two single chain Fv antibodies

<400> SEQUENCE: 9
aacagctacc gggttgtaag cgtcctcacc gtactgcacc aggactggct gaatggcaag 60
gaatacaaat gcaag 75

<210> SEQ ID NO 10

```
<211> LENGTH: 75
<212> TYPE: PRT
<213> ORGANISM: Artificial
<220> FEATURE:
<223> OTHER INFORMATION: AA sequence interlinker connecting two single
      chain Fv antibodies

<400> SEQUENCE: 10

Ala Ala Cys Ala Gly Cys Thr Ala Cys Cys Gly Gly Thr Thr Gly
1               5                   10                  15

Thr Ala Ala Gly Cys Gly Thr Cys Thr Cys Ala Cys Cys Gly Thr
                20                  25                  30

Ala Cys Thr Gly Cys Ala Cys Cys Ala Gly Gly Ala Cys Thr Gly Gly
        35                  40                  45

Cys Thr Gly Ala Ala Thr Gly Gly Cys Ala Ala Gly Gly Ala Ala Thr
    50                  55                  60

Ala Cys Ala Ala Ala Thr Gly Cys Ala Ala Gly
65                  70                  75

<210> SEQ ID NO 11
<211> LENGTH: 75
<212> TYPE: DNA
<213> ORGANISM: Artificial
<220> FEATURE:
<223> OTHER INFORMATION: Nucl Seq Bispecific antibodies interlinker
      connecting two single chain Fv antibodies

<400> SEQUENCE: 11
ttccagaatg cgctgttagt tcgttacacc aagaaagtac cccaagtgtc aactccaact    60
cttgtagagg tctca                                                    75

<210> SEQ ID NO 12
<211> LENGTH: 75
<212> TYPE: PRT
<213> ORGANISM: Artificial
<220> FEATURE:
<223> OTHER INFORMATION: AA seq bispecific antibodies interlinker
      connecting two single chain Fv antiboides

<400> SEQUENCE: 12

Thr Thr Cys Cys Ala Gly Ala Ala Thr Gly Cys Gly Cys Thr Gly Thr
1               5                   10                  15

Thr Ala Gly Thr Thr Cys Gly Thr Thr Ala Cys Ala Cys Cys Ala Ala
                20                  25                  30

Gly Ala Ala Ala Gly Thr Ala Cys Cys Cys Cys Ala Ala Gly Thr Gly
        35                  40                  45

Thr Cys Ala Ala Cys Thr Cys Cys Ala Ala Cys Thr Cys Thr Thr Gly
    50                  55                  60

Thr Ala Gly Ala Gly Gly Thr Cys Thr Cys Ala
65                  70                  75

<210> SEQ ID NO 13
<211> LENGTH: 75
<212> TYPE: DNA
<213> ORGANISM: Artificial
<220> FEATURE:
<223> OTHER INFORMATION: Nuc Seq 205C bispecific antibodies interlinker
      connecting two single chain Fv antibodies

<400> SEQUENCE: 13
gctagcgcag acgatgccaa aaaagatgca gctaaaaaag acgatgccaa aaaggacgac    60
gccaaaaaag atctg                                                    75
```

```
<210> SEQ ID NO 14
<211> LENGTH: 75
<212> TYPE: PRT
<213> ORGANISM: Artificial
<220> FEATURE:
<223> OTHER INFORMATION: AA seq 205C bispecific antibodies interlinker
      connecting two single chain Fv antibodies

<400> SEQUENCE: 14

Gly Cys Thr Ala Gly Cys Gly Cys Ala Gly Ala Cys Gly Ala Thr Gly
1               5                   10                  15

Cys Cys Ala Ala Ala Ala Ala Gly Ala Thr Gly Cys Ala Gly Cys
            20                  25                  30

Thr Ala Ala Ala Ala Ala Gly Ala Cys Gly Ala Thr Gly Cys Cys
        35                  40                  45

Ala Ala Ala Ala Gly Gly Ala Cys Gly Ala Cys Gly Cys Cys Ala
    50                  55                  60

Ala Ala Ala Ala Gly Ala Thr Cys Thr Gly
65                  70                  75
```